US009011939B2

(12) United States Patent
Lina et al.

(10) Patent No.: US 9,011,939 B2
(45) Date of Patent: Apr. 21, 2015

(54) SULPHATED ARABINOGALACTANS, APIOGALACTURONANS AND SULPHATED HETEROGLYCANS FOR TREATING DISEASES CAUSED BY THE INFLUENZA VIRUS

(75) Inventors: Bruno Lina, Lyons (FR); Olivier Ferraris, Bron (FR); Ho Hong Hai Vo, Paris (FR); François-Loïc Cosset, Lyons (FR); Judit Szecsi, Chassagny (FR); Alain Heyraud, Veurey-Voroize (FR); Hugues Lortat-Jacob, Montbonnot (FR); Julia Bartoli, La Tronche (FR); Rabia Sadir, l'Albenc (FR); Thierry Livache, Jarrie (FR); Benoît Darblade, Crolles (FR); Stéphane Havet, Saint Martin d'Heres (FR); Silvère Bonnet, Grenoble (FR)

(73) Assignees: Elicityl, Crolles (FR); Centre National de la Recherche Scientifique, Paris (FR); Institut National de la Sante et de la Recherche Medicale—I.N.S.E.R.M., Paris (FR); Commissariat a l'Energie Atomique et aux Energies Alternatives (CEA), Paris (FR)

( * ) Notice: Subject to any disclaimer, the term of this patent is extended or adjusted under 35 U.S.C. 154(b) by 88 days.

(21) Appl. No.: 13/977,780

(22) PCT Filed: Jan. 3, 2012

(86) PCT No.: PCT/FR2012/050017
§ 371 (c)(1),
(2), (4) Date: Sep. 30, 2013

(87) PCT Pub. No.: WO2012/093234
PCT Pub. Date: Jul. 12, 2012

(65) Prior Publication Data
US 2014/0023675 A1    Jan. 23, 2014

(30) Foreign Application Priority Data

Jan. 4, 2011    (FR) ...................................... 11 50049

(51) Int. Cl.
*A01N 65/00*    (2009.01)
*A61K 31/737*    (2006.01)
*A61K 31/715*    (2006.01)
*A61K 36/05*    (2006.01)
*A61K 36/888*    (2006.01)

(52) U.S. Cl.
CPC ............. *A61K 31/737* (2013.01); *A61K 31/715* (2013.01); *A61K 36/05* (2013.01); *A61K 36/888* (2013.01)

(58) Field of Classification Search
None
See application file for complete search history.

(56) References Cited

U.S. PATENT DOCUMENTS

| 6,355,684 B1 | 3/2002 | Squires |
| 2010/0015248 A1 | 1/2010 | Vanterpool |

FOREIGN PATENT DOCUMENTS

| WO | 2009/027057 | 3/2009 |
| WO | 2010/117296 | 10/2010 |
| WO | 2011/038898 | 4/2011 |

OTHER PUBLICATIONS

XP002647982, Thomson Scientific, London, GB; Oct. 14, 2010.
Damonte et al., "Antiviral activity . . . Nothogenia Fastigiata", vol. 47, No. 12, Jun. 15, 1994, XP025557482.
Chattopadhyay et al., "Polysaccharides from . . . structural features", Carbohydrate Polymers, Applied Science Publishers, Ltd., vol. 68, No. 3, Mar. 13, 2007, XP005919345.
Kim et al., "Immunological Activity . . . Placebo-controlled Trial", XP002647983, Alternative Medicine Review: A Journal of Clinical Therapeutic, Apr. 2002, vol. 7, No. 2.
Hosoya et al., "Differential Inhibitory . . . Envelope Glycoproteins", Antimicrobial Agents and Chemotherapy, vol. 35, No. 12, 1991, pp. 2515-2520 XP002647984.
Popov et al., "Isolation, Characterization . . . Pectic Polysaccharides", vol. 40, No. Suppl. 1, pp. 1-22, 46-71, XP002647985, 2006.
Choi et al., "Immunomodulating activity of . . . in vitro", XP002647986, Journal of Medicinal Food, Jan. 4, 2005, pp. 446-453, vol. 8, No. 4.
Ohta et al., "Isolation . . . antiviral effect", XP018024654, Oct. 1, 2009, vol. 31, No. 5.

*Primary Examiner* — Michael Meller
(74) *Attorney, Agent, or Firm* — Clark & Brody

(57) ABSTRACT

The present invention relates to polysaccharides selected from sulphated arabinogalactans, apiogalacturonans and sulphated heteroglycans intended to be used as a drug for the preventive or curative treatment of an influenza virus, as well as to the pharmaceutical compositions including, in particular in combination with at least one pharmaceutically acceptable carrier:
either an extract of *Codium fragile*, including sulphated arabinogalactans,
or an extract of *Zostera marina* or *Lemna minor*, including apiogalacturonans,
or an extract of *Caulerpa racemosa*, including sulphated heteroglycans.

18 Claims, 25 Drawing Sheets

Figure 1:
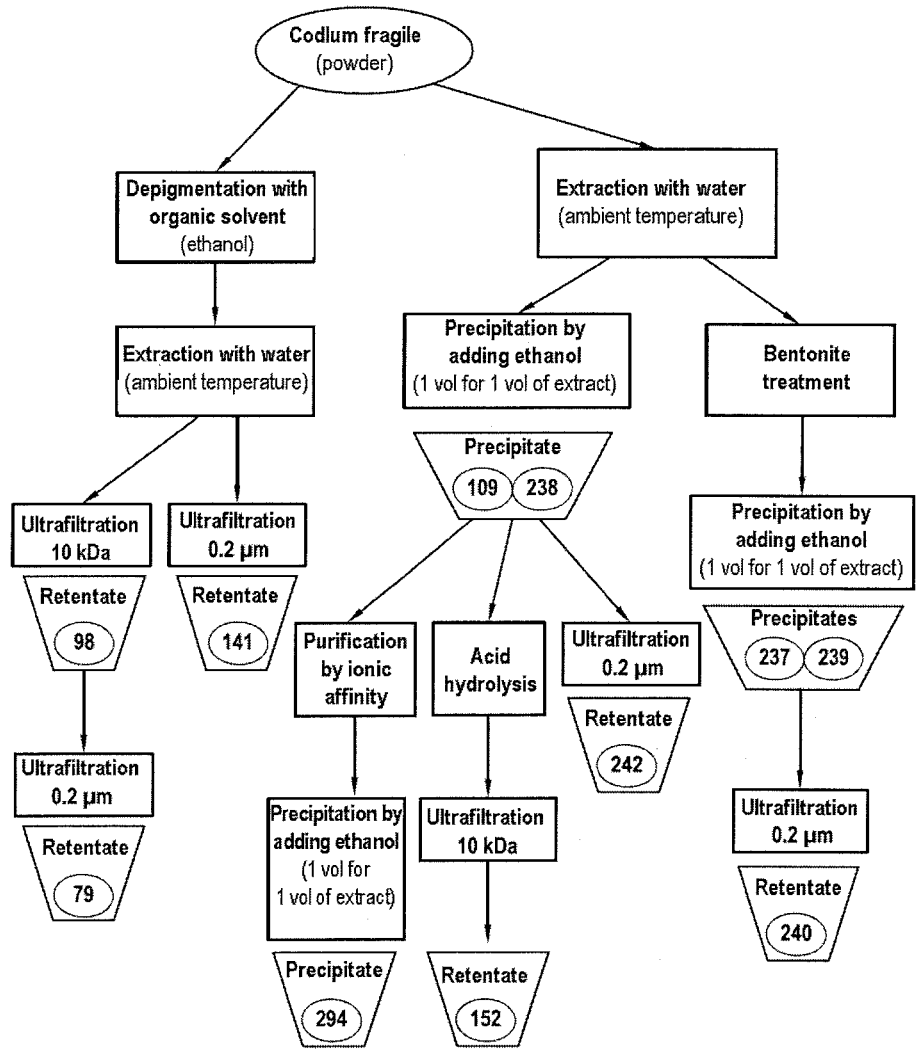

FIG.30 Inhibition of influenza A H5N1 VLP entry

FIG.31 Inhibition of influenza A H7N1 VLP entry

FIG.32
- Infected and noninfected
- Infected and treated with the polysaccharide 295
- Infected and treated with the polysaccharide 294
- Infected and treated with the polysaccharide 296
- Noninfected and treated with the polysaccharides Separated polysaccharides | Crude polysaccharides Interactions of carrageenans with HA1

FIG.40

FIG.42

** : condition at 34°C, under 5% $CO_2$

* : condition at 4°C

□ : Virus inoculation time o : 152 addition time    ↓: washing point

SULPHATED ARABINOGALACTANS, APIOGALACTURONANS AND SULPHATED HETEROGLYCANS FOR TREATING DISEASES CAUSED BY THE INFLUENZA VIRUS

The present invention relates to the technical field of influenza viruses. More specifically, the invention relates to the use of certain polysaccharides, as a medicament for the preventive or curative treatment of an influenza virus.

Influenza is a respiratory infection caused by influenza viruses. It is observed throughout the world and reappears each year in winter epidemic waves. At the current time, it is the second most common cause of infectious mortality after pneumonia. The influenza viruses responsible for pathological conditions in humans are the type A and B influenza viruses. While type B influenza viruses circulate in lineage form, type A influenza viruses are classified intoviral subtypes according to the antigenic properties of the two major surface glycoproteins, hemagglutinin (HA) and neuraminidase (NA). The viruses which circulate in humans and are responsible for seasonal epidemics are the A (H1N1) and A (H3N2) viruses.

Vaccination is, for the moment, the only efficient means for protecting populations against influenza viruses. Nevertheless, alternative solutions, in the form of antiviral medicaments, are the subject of numerous investigations.

Document WO 2009/027057 describes the use of carrageenans in a pharmaceutical composition for the prophylaxis and treatment of respiratory viral diseases caused by orthomyxoviruses, and in particular influenza A and B viruses.

The publication by M. Hosoya et al. in Antimicrobial agents and chemotherapy, 1991, 35(12), 2515-2520 studies the effect of polysaccharides selected from:
dextran sulfate: sulfated glucose polymer
heparin: polymer formed by the linking of disaccharide units composed of a sulfated iduronic acid and a sulfated galactosamine
pentosan polysulfate: sulfated D-xylan polymer
mannan sulfate: sulfated mannan polymer.

However, just because certain polysaccharides exhibit an activity with respect to certain viruses, and in particular against the influenza virus, this does not mean that the same activity can be envisioned for another polysaccharide, quite the contrary, as will be demonstrated in the examples with nonsulfated arabinogalactans and ulvans.

Patent application US 2010/0015248 provides a composition for the treatment of colds and influenza, which comprises a mixture of acetaminophen, diphenylhydramine, dextromethorphan, arabinogalactan, vitamin C, zinc, olive oil extract, resveratrol and elderberry extract. It is specified, in that document, that the arabinogalactan, vitamin C and zinc are present in order to stimulate the immune system. The olive oil extract, resveratrol and elderberry extract are used as antiviral agents. The acetaminophen, diphenylhydramine and dextromethorphan, for their part, are used to relieve influenza symptoms.

Document WO 98/11778 describes medicinal compositions for the treatment of various viral diseases, comprising an inhibitor of the microbial infection responsible for the disease to be treated, in the form of an isolate of various plants. The influenza virus is cited among a list of various viral infections, but the invention is instead directed toward the treatment of herpesvirus, to which all the examples and results relate.

In this context, the present invention is based on the demonstration by the inventors, totally unexpectedly, that certain particular polysaccharides exhibit an antiviral activity against influenza viruses. The subject of the invention is therefore polysaccharides selected from sulfated arabinogalactans, apiogalacturonans and heteroglycan sulfates, for use thereof as a medicament in the preventive or curative treatment of a disease cause by an influenza virus.

The term "treatment" denotes any therapeutic measure which is prophylactic or suppressive with respect to a disease caused by an influenza virus, resulting in a desirable clinical effect or in any beneficial effect, including in particular the suppression or reduction of one or more symptoms, or the regression, slowing down or ceasing of the progression of the disease which is associated therewith. The diseases caused by an influenza virus are generally called influenzas.

In particular, the invention relates to polysaccharides selected from sulfated arabinogalactans, apiogalacturonans and heteroglycan sulfates, for use thereof as an antiviral agent against the influenza virus in a medicament intended for the treatment or prevention of an influenza virus. In other words, the present invention relates to the use of a polysaccharide selected from sulfated arabinogalactans, apiogalacturonans and heteroglycan sulfates, for preparing a medicament intended for the preventive or curative treatment of an influenza virus. In the medicament, the polysaccharide selected from sulfated arabinogalactans, apiogalacturonans and heteroglycan sulfates acts as an active ingredient, i.e. it is used for its antiviral activity against influenza viruses. According to one particular embodiment, in the medicament or the pharmaceutical composition containing at least one polysaccharide selected from sulfated arabinogalactans, apiogalacturonans and heteroglycan sulfates, the antiviral activity against influenza viruses is at least 70%, preferably at least 90% and preferentially at least 95% provided by the sulfated arabinogalactans, apiogalacturonans or heteroglycan sulfates present. According to one particular embodiment, said medicament or pharmaceutical composition containing at least one polysaccharide selected from sulfated arabinogalactans, apiogalacturonans and heteroglycan sulfates does not contain any compound, other than the sulfated arabinogalactan(s), the apiogalacturonans and the heteroglycan sulfates, exhibiting a significant antiviral activity. On the other hand, it is possible to use, in one and the same composition, a combination of polysaccharides selected from sulfated arabinogalactans, apiogalacturonans and heteroglycan sulfates. The expression "compound exhibiting a significant antiviral activity" is intended to mean a compound which leads to a significant inhibition of the replication of the target virus; for example, an inhibition of at least 25%, preferably of at least 50% and preferentially of at least 80% at a concentration of 250 µg/ml, in a test for inhibition of the replication of the target influenza virus, such as those in particular described in section 1 of the examples hereinafter. In the context of the invention, the inventors have demonstrated that polysaccharides belonging to the sulfated arabinogalactan, apiogalacturonan or heteroglycan sulfate family have an influence on the replication cycle of influenza viruses and make it possible to inhibit the infection of infection-sensitive cells. It has also been demonstrated that these sugars make it possible to inhibit the entry of influenza viruses into virus-like particles (VLPs). The inhibitory activity of the polysaccharides belonging to the sulfated arabinogalactan, apiogalacturonan or heteroglycan sulfate family has been found to be equivalent to, or even greater than, the carrageenans already described in the literature for this type of activity. On the other hand, other polysaccharides of the ulvan family have been found to be inactive, demonstrating the specific properties of the polysaccharides selected in the context of the invention. The inventors have also demonstrated that, unlike sulfated arabinogalactans, nonsulfated arabinogalactans, such as those extracted from larch bark (in particular studied in WO 2010/117296, Alternative Medecine Reviews, 2002, vol. 7, No. 2, 138-149, J. Med. Food, 2005, 8(4), 446-453 and WO 2011/138898), do not exhibit any activity, as will become apparent in the examples which follow.

Sulfated arabinogalactans are water-soluble sulfated polysaccharides composed of galactose units linked to one another via beta-1,3-glycosidic linkages. This main chain can have branches of arabinose or galactose units via alpha-1,6-glycosidic linkages. These units can have several arabinose and/or galactose units linked to one another via 1,3- or 1,6-glycosidic linkages. The arabinoses or galactoses can have sulfations on secondary alcohol groups. The arabinose/galactose ratio is preferably in the range of from 3/7 to 2/1, and corresponds, for example, to 1/1, 1/2 or 2/1.

In the context of the invention, use will preferably be made of sulfated arabinogalactans having a size which is in the range of from 1000 $2 \times 10^6$ g/mol, preferably in the range of from 3000 to $1.1 \times 10^6$ g/mol, and/or a corresponding average load of from 2% to 50% and preferably from 5% to 40% of sulfate groups.

Apiogalacturonans are water-soluble polysaccharides which can be sulfated, formed by a linear chain of galacturonic acid units linked to one another via alpha-1,4-glycosidic linkages. This main chain can have apiose units linked via beta-1,2-glycosidic linkages. These units can have several apiose units linked to one another via beta-1,5-glycosidic linkages.

In the context of the invention, use will preferably be made of apiogalacturonans having a size which is in the range of from 10 000 to $10^6$ g/mol, preferably in the range of from 50 000 to 700 000 g/mol, and/or a corresponding average load of from 2% to 20% and preferably from 4% to 12% of sulfate groups.

The sulfated heteroglycans used in the context of the invention are water-soluble polysaccharides formed by a linear chain of alpha-1,3-linked and terminally-linked galactose units, of 1,4-linked xylose units and of 1,4-linked arabinose units. The galactose units can have sulfations in the C6 position and the arabinose units can have sulfations in the C3 position.

In the context of the invention, use will preferably be made of sulfated heteroglycans having a size which is in the range of from 500 000 to $5 \times 10^6$ g/mol and, for example, approximately $10^6$ g/mol, and/or a corresponding average load of from 5% to 30% and preferably from 13% to 22% of sulfate groups.

The sulfated arabinogalactans, apiogalacturonans and heteroglycan sulfates used in the context of the invention can be prepared by chemical synthesis or will preferably be extracted from a natural source, such as algae or plants. In particular, they can correspond:
- to an extract of *Codium fragile, Codium vermilara* or *Codium cylindricum* comprising sulfated arabinogalactans,
- to an extract of *Zostera marina* or of *Lemna minor* comprising apiogalacturonans,
- to an extract of *Caulerpa racemosa* comprising heteroglycan sulfates.

Any extraction method well known to those skilled in the art may be used. In particular, methods for extracting complex sugars using aqueous or organic solvents, optionally followed by purification by selective precipitation, ionic interactions, filtrations, etc., may be used. By way of example, an extraction comprising a step of extraction with water and a step of precipitation with an alcohol such as ethanol may be used.

It is, for example, possible to use methods of extraction from *Codium fragile* in an aqueous medium at ambient temperature in order to preserve the sulfated arabinogalactans. In particular, the methods detailed in the examples hereinafter, or analogous methods, may be used.

The polysaccharides selected from sulfated arabinogalactans, apiogalacturonans and heteroglycan sulfates, and in particular those previously described, can be used for the curative or preventive treatment of any type of influenza virus. The term "influenza virus" is intended to denote all influenza viruses, and in particular human, avian, equine, porcine and feline influenza viruses. Said influenza viruses can be selected from types A, B and C. In particular, the influenza virus may be of type A and in particular correspond to the strains of subtype H1N1, H2N2, H3N2, H4N2, H4N6, H5N1, H5N2, H7N1, H7N7 and H9N2. According to one particular embodiment, the influenza virus is selected from type B, A-H5N1, A-H7N1 and A-H3N2 viruses.

The subject of the present invention is also the pharmaceutical compositions administrable to animals, and in particular to human beings, comprising, in combination with at least one pharmaceutically acceptable excipient according in particular to the European Pharmacopea 7th edition:
- either an extract of *Codium fragile, Codium vermilara* or *Codium cylindricum* comprising sulfated arabinogalactans,
- or an extract of *Zostera marina* or of *Lemna minor* comprising apiogalacturonans,
- or an extract from *Caulerpa racemosa* comprising heteroglycan sulfates.

The excipients present in the medicaments and pharmaceutical compositions according to the invention are selected according to the pharmaceutical form and the mode of administration desired. In the pharmaceutical compositions of the present invention for oral, sublingual, subcutaneous, intramuscular, intravenous, intracartilage, topical, intratracheal, intranasal, transdermal, rectal or intraocular administration, the polysaccharides can be administered in unit administration forms, as a mixture with conventional pharmaceutical carriers, to animals and to human beings for the prophylaxis or the treatment of the above diseases. The suitable unit administration forms include oral forms, such as tablets, gel capsules, powders, granules and oral solutions or suspensions, sublingual, buccal, intratracheal or intranasal administration forms, subcutaneous, intramuscular, intracartilage or intravenous administration forms and rectal administration forms. For topical application, the compounds according to the invention can be used in creams, ointments or lotions.

The medicament or composition generally contains a therapeutically effective amount of polysaccharides selected from sulfated arabinogalactans, apiogalacturonans and heteroglycan sulfates. The expression "therapeutically effective amount" denotes any amount of a composition which improves one or more of the characteristic parameters of the affection treated. In order to obtain the desired effect, the dose of polysaccharide ranges, for example, between 0.001 and 100 mg per kg of body weight and per day. Nevertheless, in the context of the invention, the pharmaceutical compositions also include homeopathic compositions.

When a solid composition is prepared in tablet form, the main active ingredient is mixed with a pharmaceutical vehicle, such as gelatin, starch, lactose, magnesium stearte, talc, gum Arabic, or the like. The tablets may be coated with sucrose, with a cellulose-based derivative, or with other suitable materials, or else they can be treated such that they have a sustained or delayed activity and that they continuously release a predetermined amount of active ingredient.

A preparation of gel capsules is obtained by mixing the active ingredient with a diluent and by pouring the mixture obtained into soft or hard gel capsules.

The pharmaceutical compositions containing a polysaccharide in accordance with the invention can also be in liquid form, for example solutions, emulsions, suspensions or syrups, and in particular in a form suitable for oral or intranasal administration, for example. The suitable liquid carriers can be, for example, water, organic solvents such as glycerol or glycols, and mixtures thereof, in varied proportions, in water.

A preparation in syrup or elixir form or for administration in the form of drops can contain the active ingredient together with a sweetener, preferably a calorie-free sweetener, methylparaben and propylparaben as antiseptic, and also a flavoring and a suitable colorant. The water-dispersible powders or granules can contain the active ingredient as a mixture with dispersants or wetting agents, or suspension agents, for instance polyvinylpyrrolidone, and also with sweeteners or flavor enhancers.

It is possible for the medicaments or compositions comprising at least one polysaccharide selected from sulfated arabinogalactans, apiogalacturonans and heteroglycan sulfates to be for human or veterinary use. In particular, in the case of the treatment of chickens, the polysaccharide may be in a feed additive.

Generally, the same variants apply, mutatis mutandis, to the medicaments, compositions and uses employing the polysaccharides selected from sulfated arabinogalactans, apiogalacturonans and heteroglycan sulfates.

According to one particular embodiment, the antiviral medicaments and compositions against the influenza virus, according to the invention, do not contain olive oil, nor resveratrol, nor extract of elderberry, in particular when they contain an arabinogalactan as previously defined.

According to another of its aspects, the present invention also relates to a method for treating human beings or animals, and in particular chickens, comprising the administration and the use of a polysaccharide selected from sulfated arabinogalactans, apiogalacturonans and heteroglycan sulfates for preventively or curatively combating a disease caused by an influenza virus.

According to another of its aspects, the present invention also relates to the use of a polysaccharide selected from sulfated arabinogalactans, apiogalacturonans and heteroglycan sulfates in a food composition in which said polysaccharide is used for preventively or curatively combating a disease caused by an influenza virus.

According to one particular embodiment, the food composition comprises:
- either an extract of *Codium fragile*, *Codium vermilara* or *Codium cylindricum* comprising sulfated arabinogalactans,
- or an extract of *Zostera marina* or of *Lemna minor* comprising apiogalacturonans,
- or an extract of *Caulerpa racemosa* comprising heteroglycan sulfates.

According to one particular embodiment which can be combined with the previous one, the food composition does not contain olive oil, nor resveratrol, nor extract of elderberry.

All the implementation variants, with regard in particular to the definitions, previously described in relation to the medicaments and the pharmaceutical compositions, of the sugars, of the extracts and extraction methods for obtaining them and of the influenza viruses targeted apply, mutatis mutandis, to the food compositions and to the treatment methods. The term "food composition" is intended to mean, for example, any type of functional food, or of food products in the form of yoghurt or milk drink in particular, intended for humans or for animals.

The examples hereinafter, with reference to the appended figures, make it possible to illustrate the invention but are in no way limiting in nature.

FIG. 1 presents diagrammatically the various methods for obtaining the various *Codium fragile* extracts tested in the examples.

Figure 2:
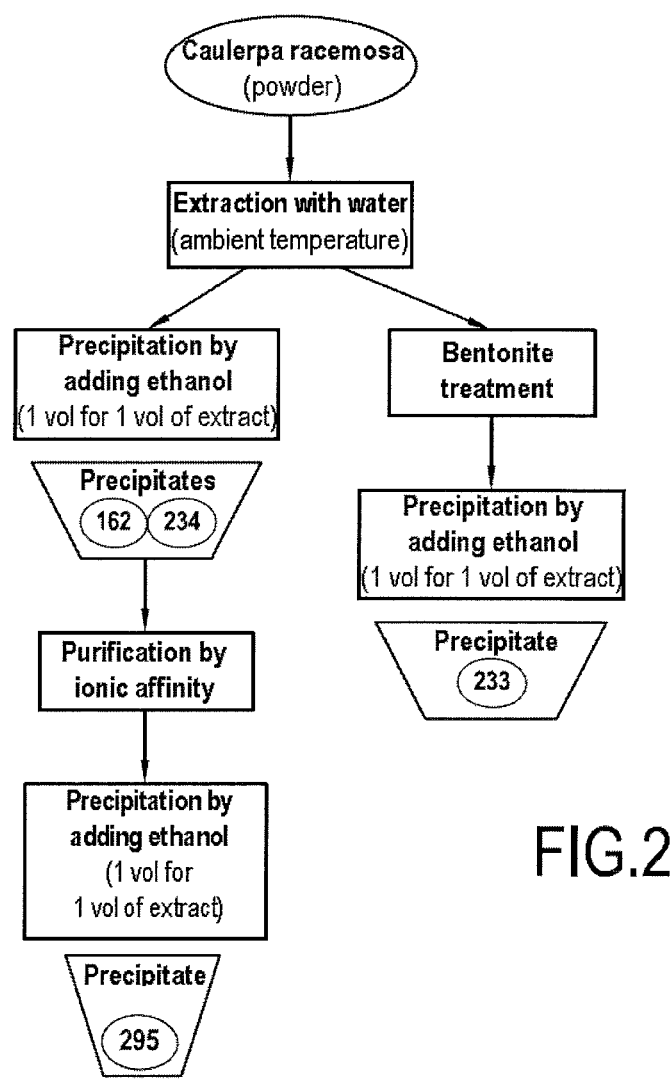

FIG. 2 presents diagrammatically the various methods for obtaining the various *Caulerpa racemosa* extracts tested in the examples.

Figure 3:
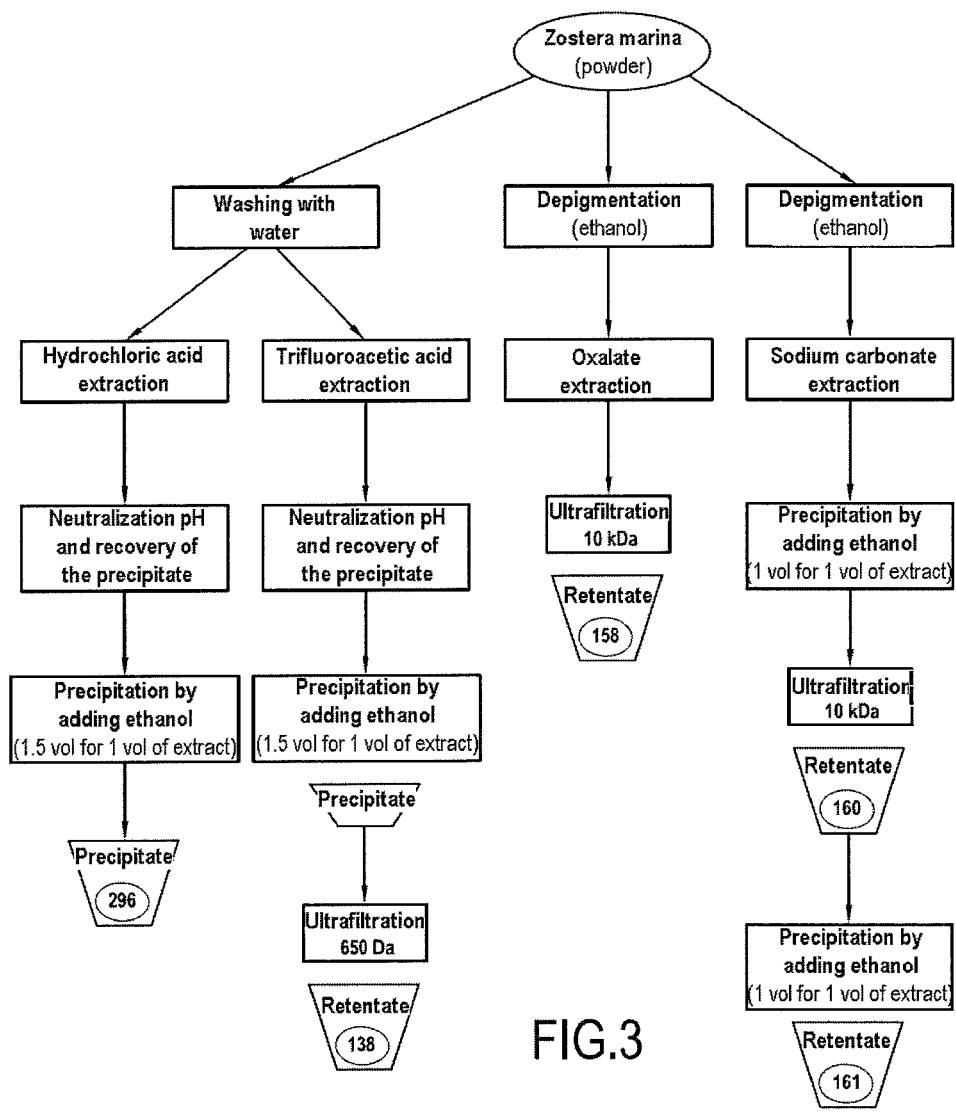

FIG. 3 presents diagrammatically the various methods for obtaining the various *Zostera marina* extracts tested in the examples.

Figure 4:
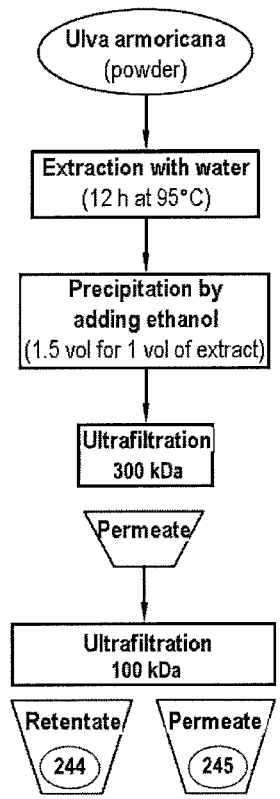

FIG. 4 presents diagrammatically the various methods for obtaining the various *Ulva armoricana* extracts tested in the examples.

Figure 5:
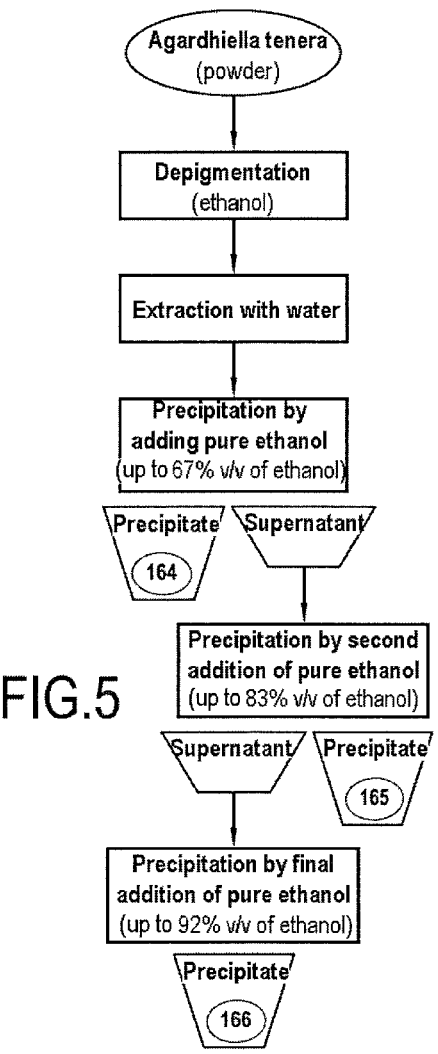

FIG. 5 presents diagrammatically the various methods for obtaining the various *Agardhiella tenera* extracts tested in the examples.

Figure 6:
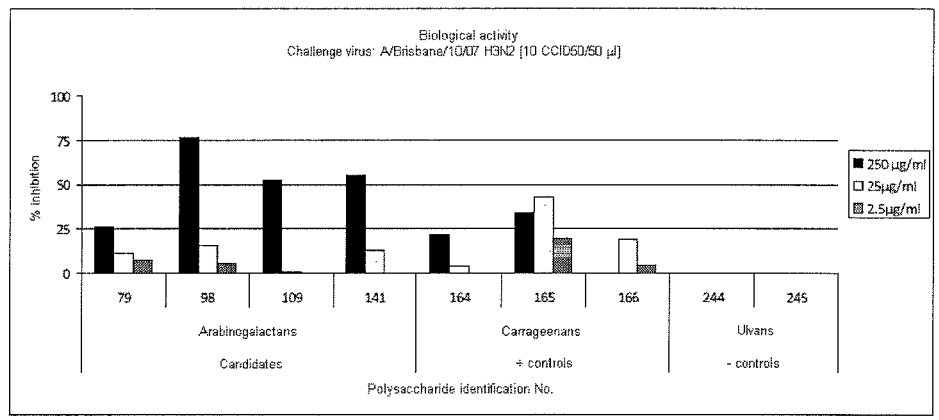
Figure 7:
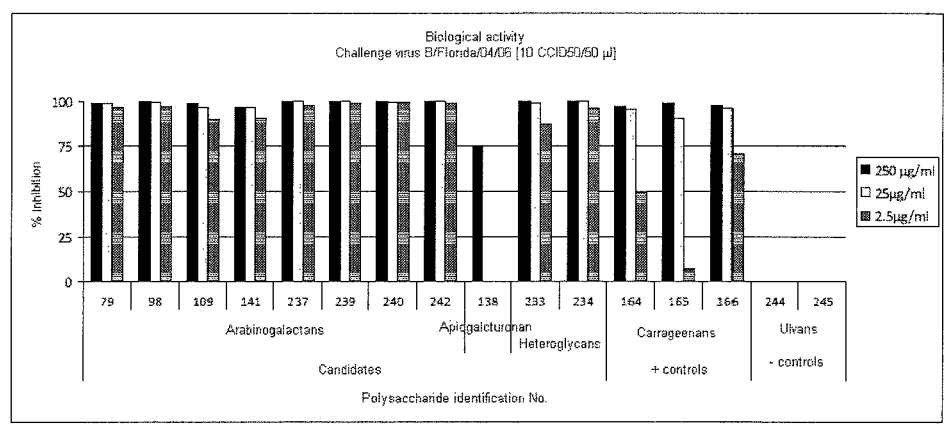

FIGS. 6 and 7 present the results of biological activity of various polysaccharides tested on A/Brisbane/10/2007 H3N2 and B/Florida/4/06 viruses respectively.

Figures 8, 9:
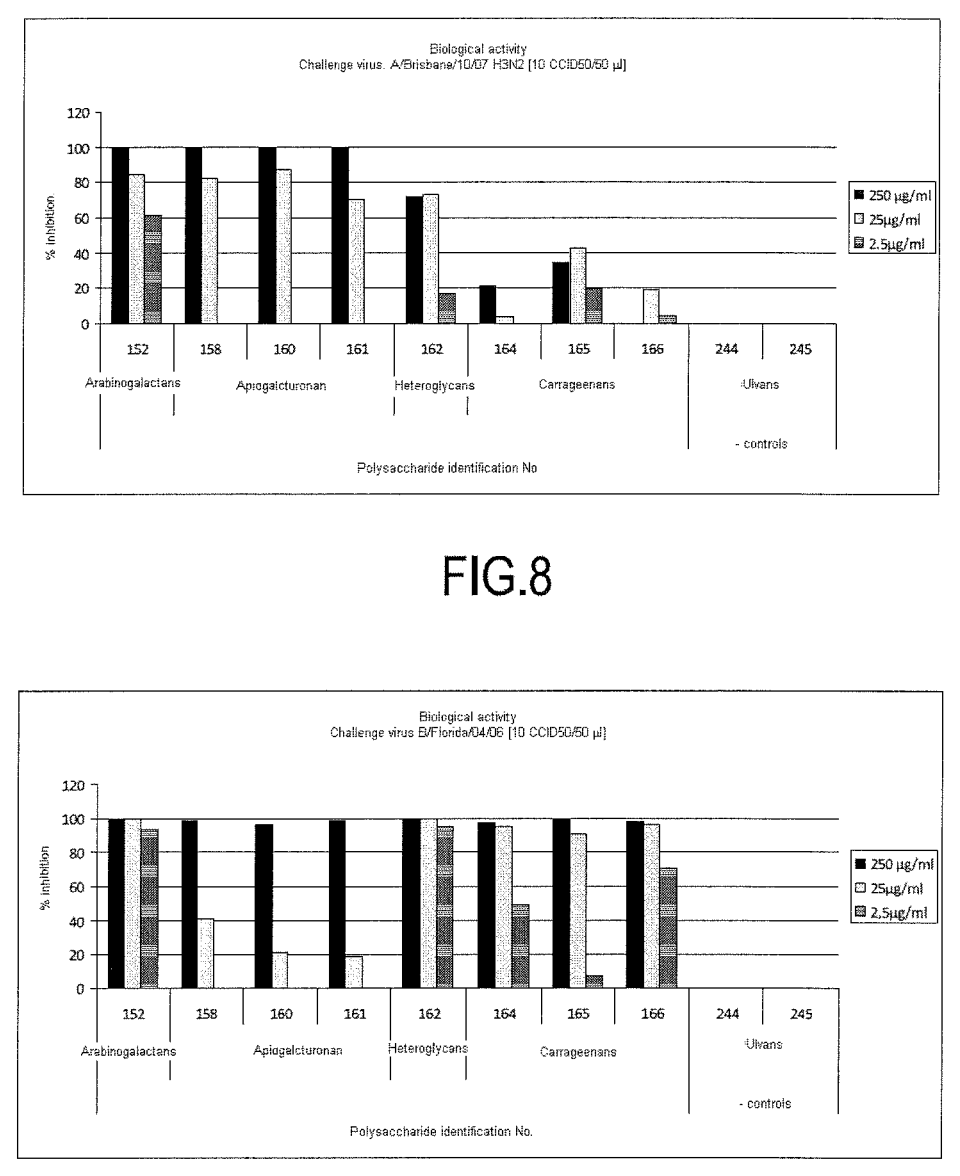

FIGS. 8 and 9 present the results of biological activity of other various polysaccharides tested on A/Brisbane/10/2007 H3N2 and B/Florida/4/06 viruses respectively.

Figure 10:
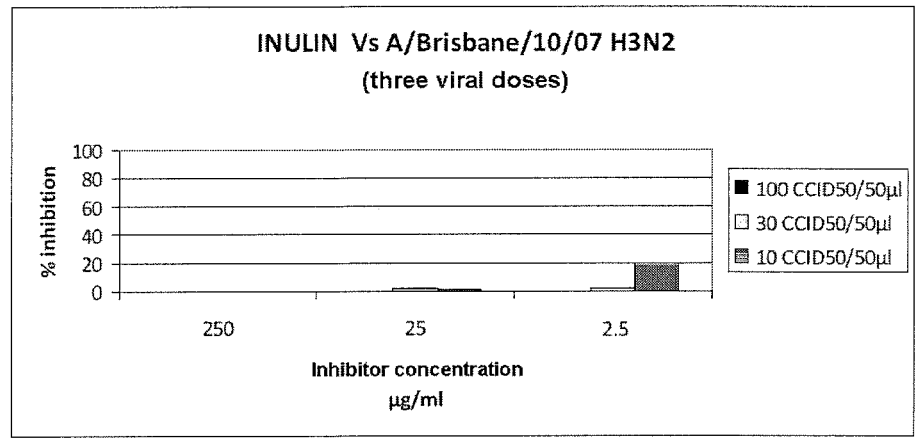
Figure 11:
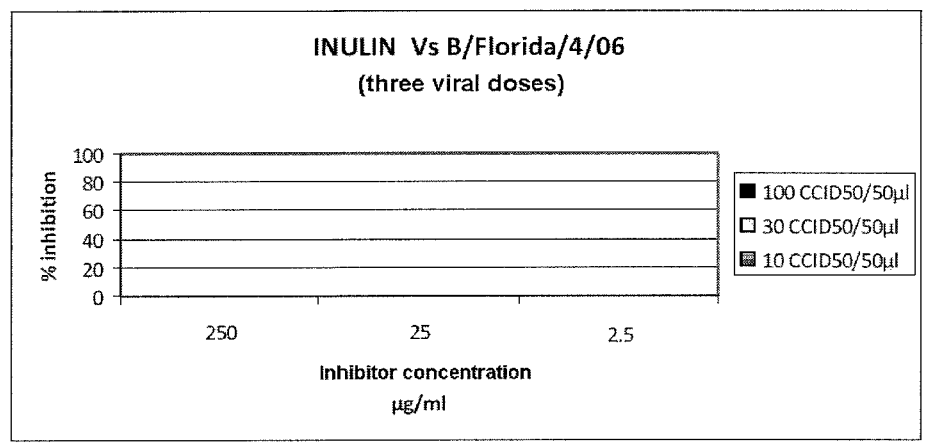

FIGS. 10 and 11 present the results of biological activity of inulin on A/Brisbane/10/2007 H3N2 and B/Florida/4/06 viruses respectively.

Figure 12:
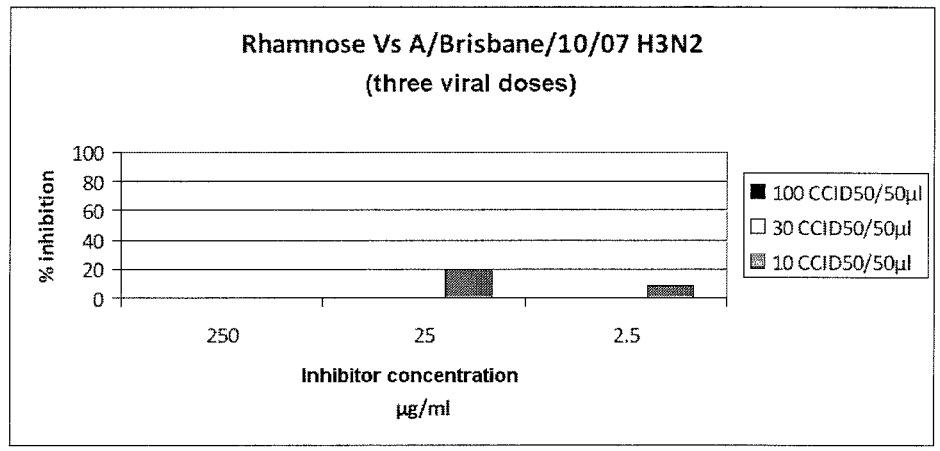
Figure 13:
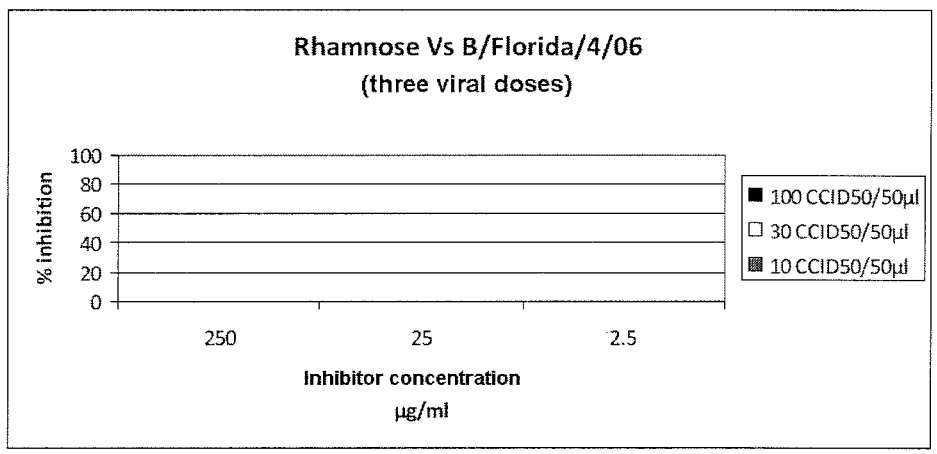

FIGS. 12 and 13 present the results of biological activity of rhamnose on A/Brisbane/10/2007 H3N2 and B/Florida/4/06 viruses respectively.

Figure 14:
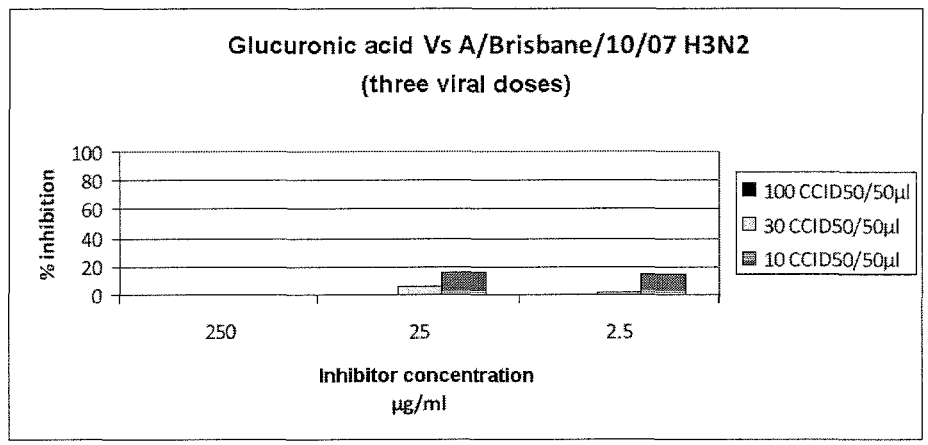
Figure 15:
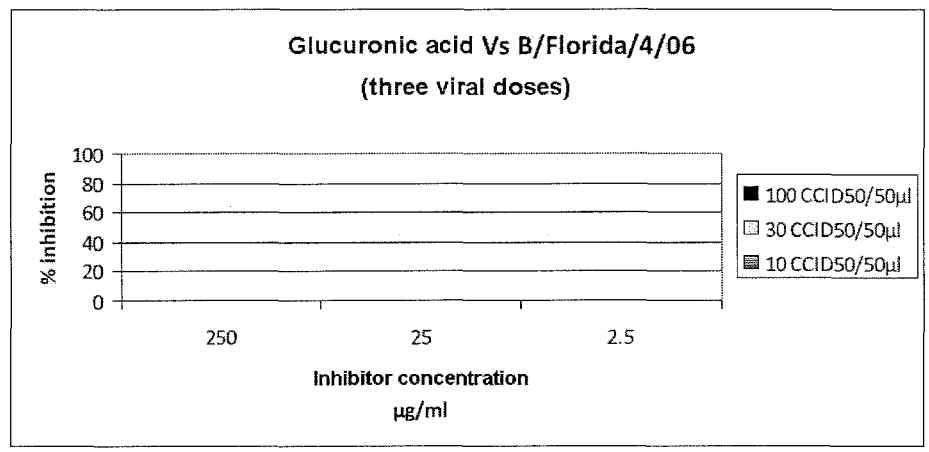

FIGS. 14 and 15 present the results of biological activity of glucuronic acid on A/Brisbane/10/2007 H3N2 and B/Florida/4/06 viruses respectively.

Figures 16, 17:
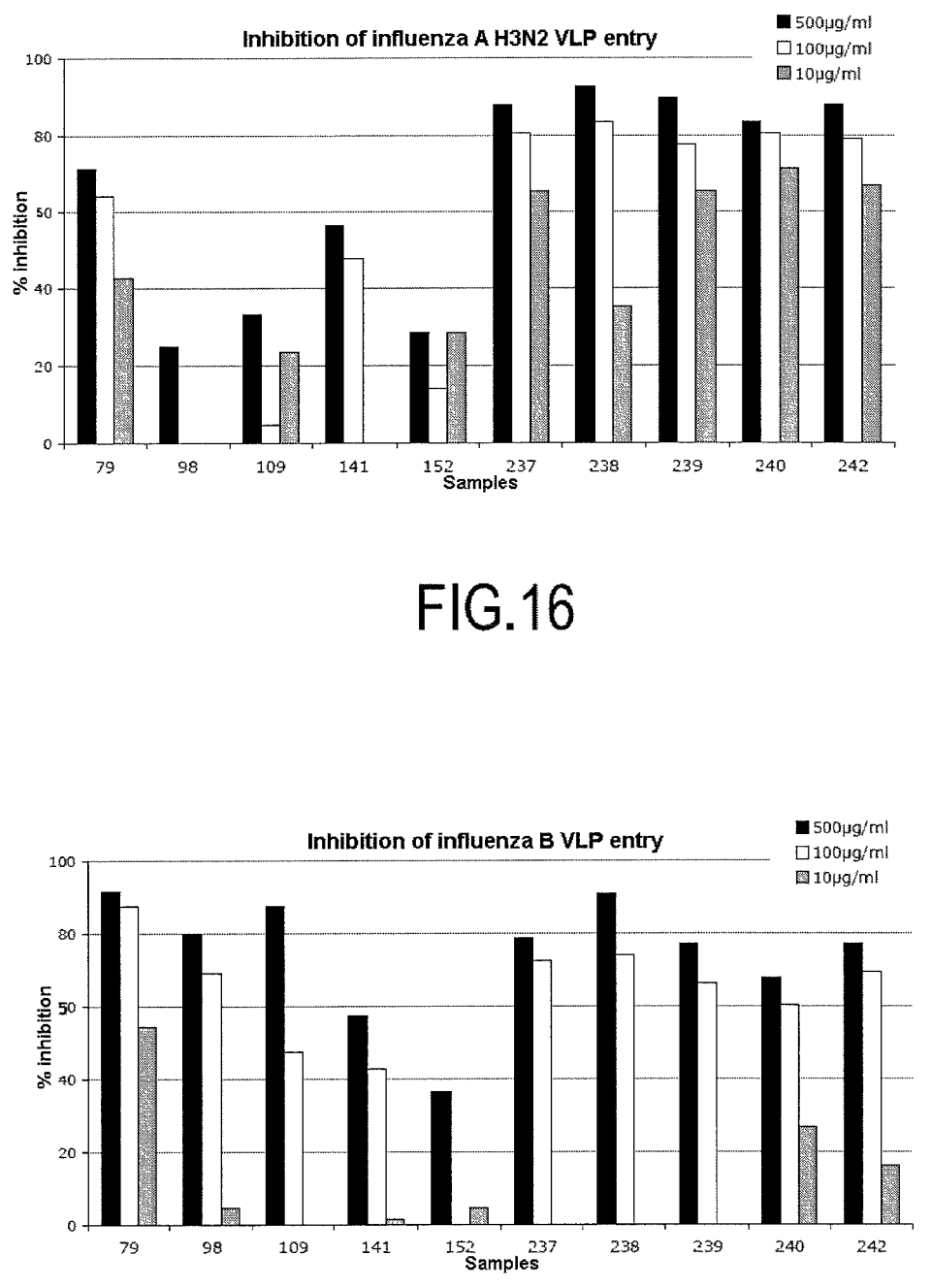

FIG. 16 presents the inhibitory activity of the sulfated arabinogalactans tested in the examples on the entry of influenza A H3N2 VLPs.

FIG. 17 presents the inhibitory activity of the sulfated arabinogalactans tested in the examples on the entry of influenza B VLPs.

Figure 18:
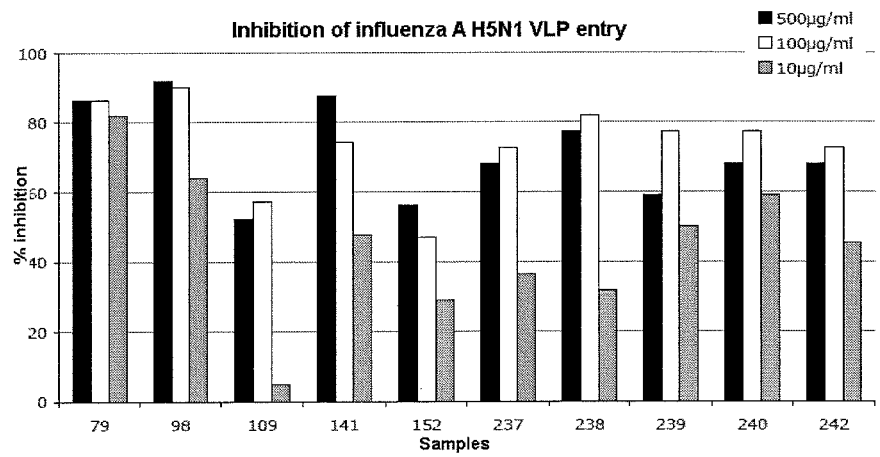

FIG. 18 presents the inhibitory activity of the sulfated arabinogalactans tested in the examples on the entry of influenza A H5N1 VLPs.

Figure 19:
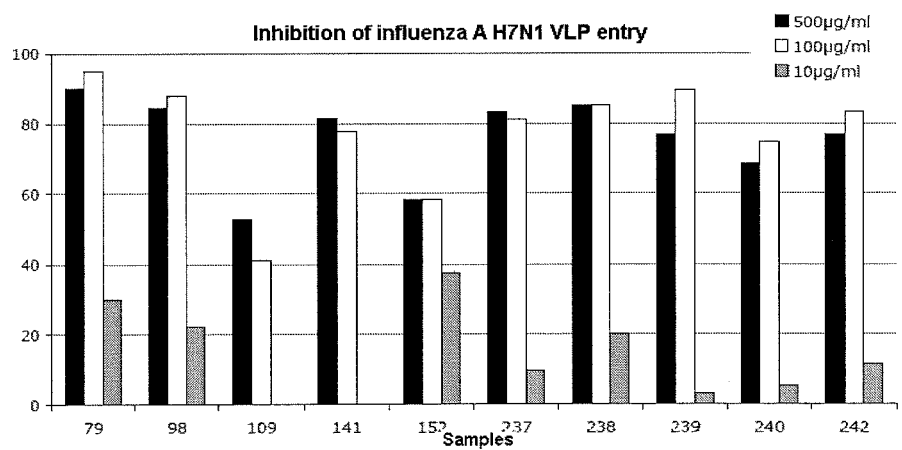

FIG. 19 presents the inhibitory activity of the sulfated arabinogalactans tested in the examples on the entry of influenza A H7N1 VLPs.

Figures 20, 21:
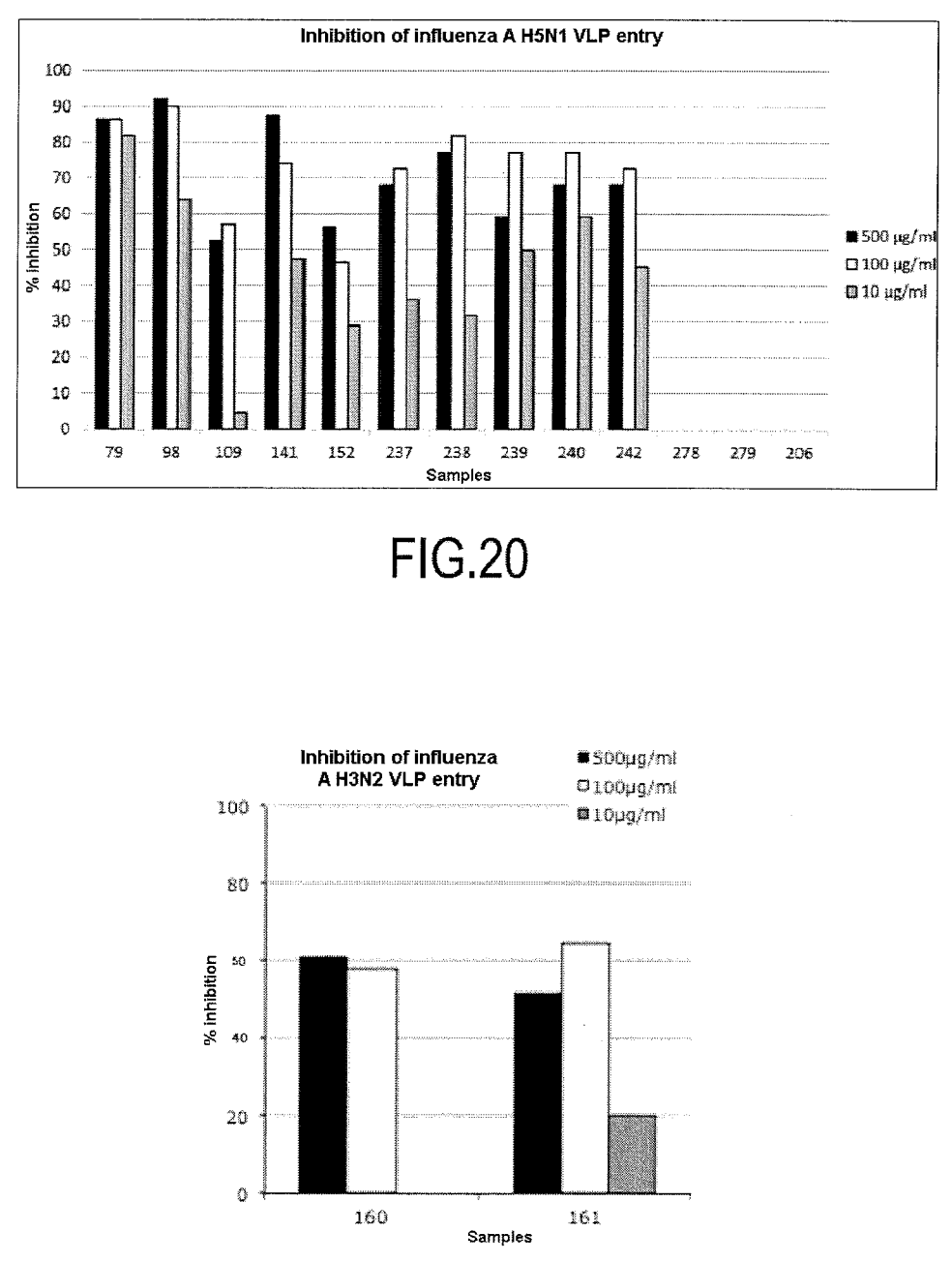

FIG. 20 shows the % inhibitions of influenza A H5N1 VLP entry that were obtained with the sulfated arabinogalactans extracted from *Codium fragile* (79, 98, 109, 141, 152, 237, 238, 239, 240, 242) in comparison with those obtained in the case of two arabinogalactans extracted from *Codium fragile*, but which were desulfated (278, 279) and of a nonsulfated arabinogalactan extracted from larch (206)

FIG. 21 presents the inhibitory activity of the apiogalacturonans 160 and 161 tested on the entry of influenza A H3N2 VLPs, at concentrations of 10, 100 and 100 µg/ml.

Figures 22, 23:
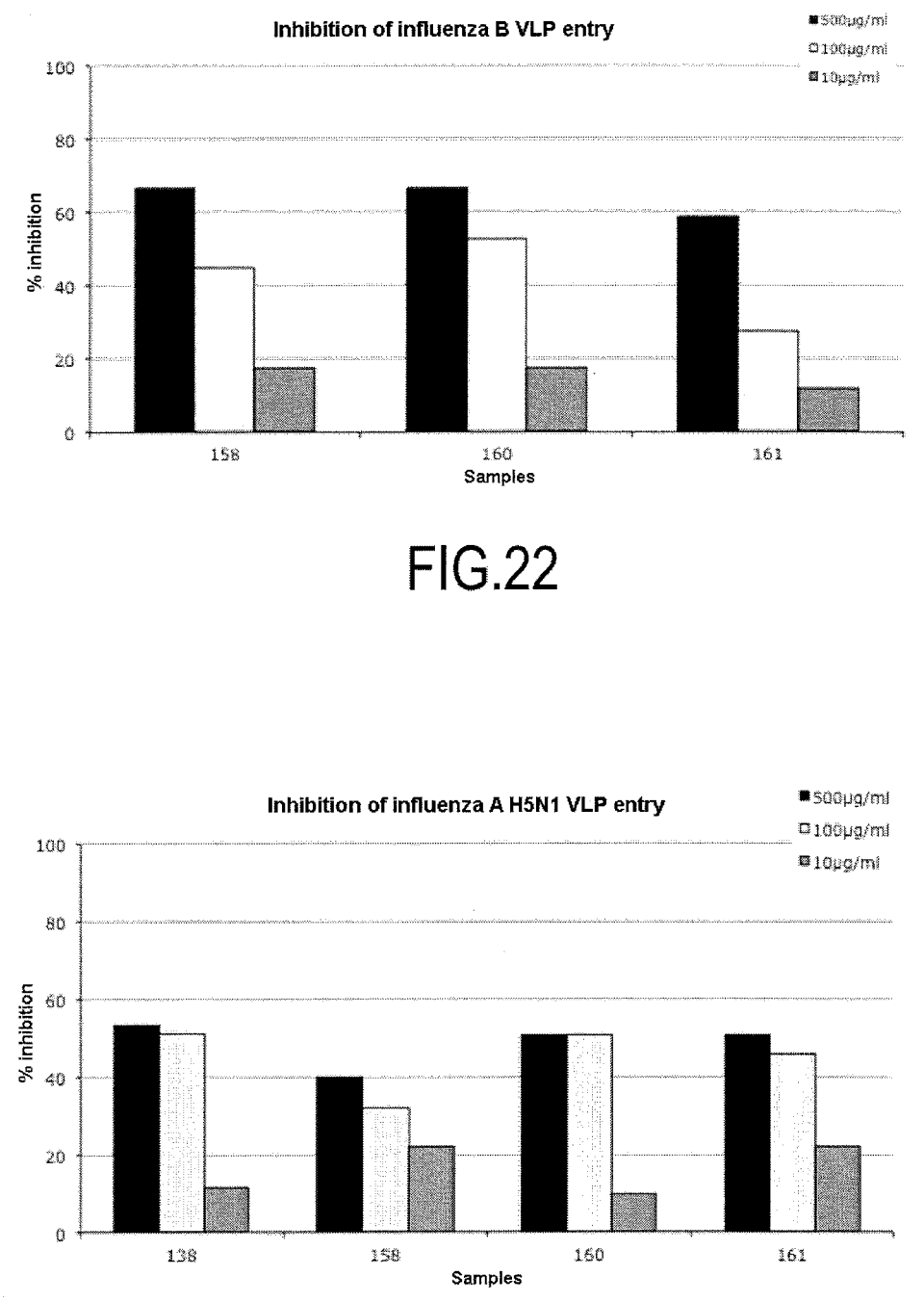

FIG. 22 presents the inhibitory activity of the apiogalacturonans 158, 160 and 161 tested on the entry of influenza B VLPs, at concentrations of 10, 100 and 500 µg/ml.

FIG. 23 presents the inhibitory activity of the apiogalacturonans 138, 158, 160 and 161 tested on the entry of influenza A H5N1 VLPs, at concentrations of 10, 100 and 500 µg/ml.

Figures 24, 25:
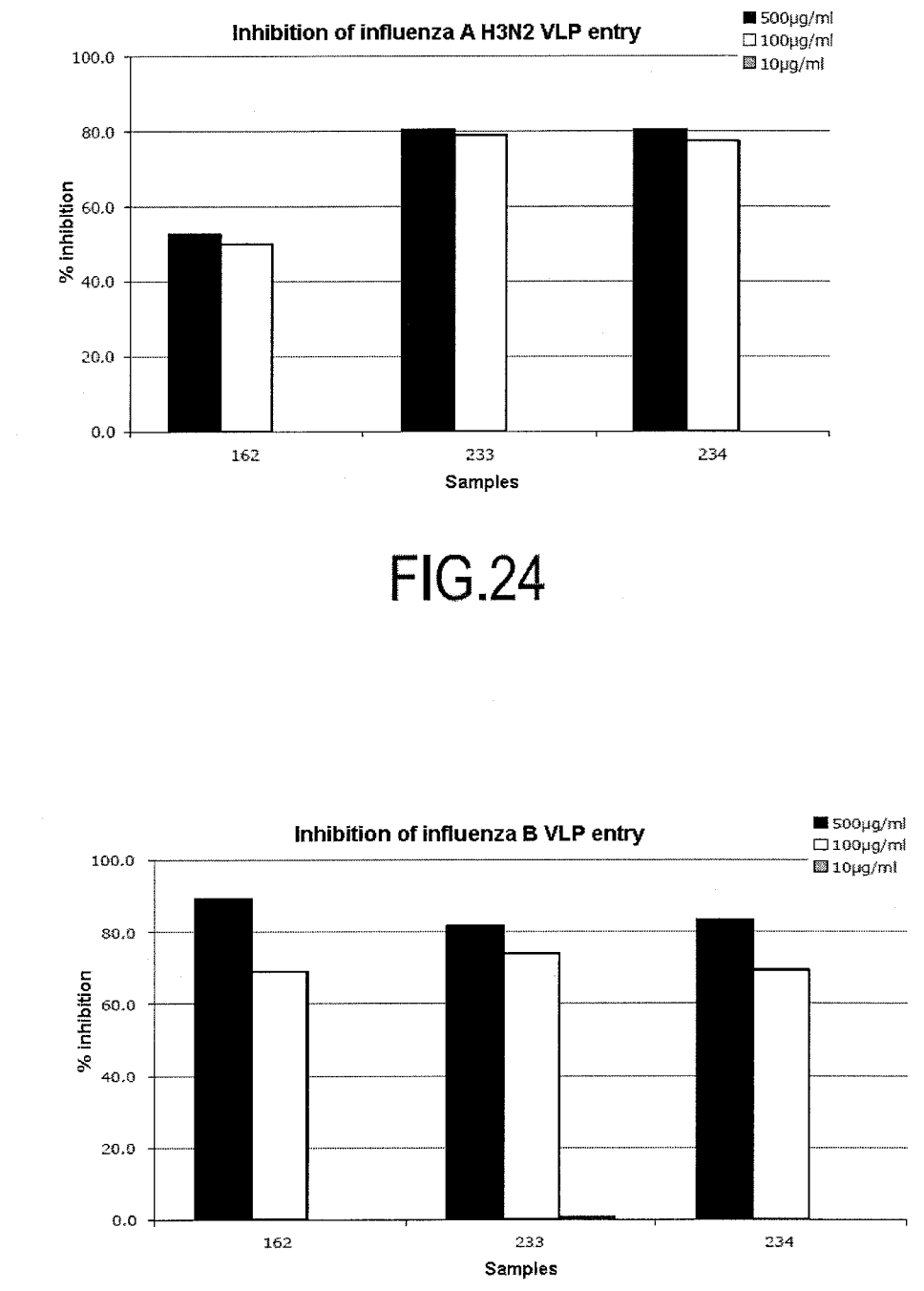

FIG. 24 presents the inhibitory activity of the sulfated heteroglycans 162, 233 and 234 tested on the entry of influenza A H3N2 VLPs, at concentrations of 10, 100 and 500 µg/ml.

FIG. 25 presents the inhibitory activity of the sulfated heteroglycans 162, 233 and 234 tested on the entry of influenza B VLPs, at concentrations of 10, 100 and 500 µg/ml.

Figures 26, 27:
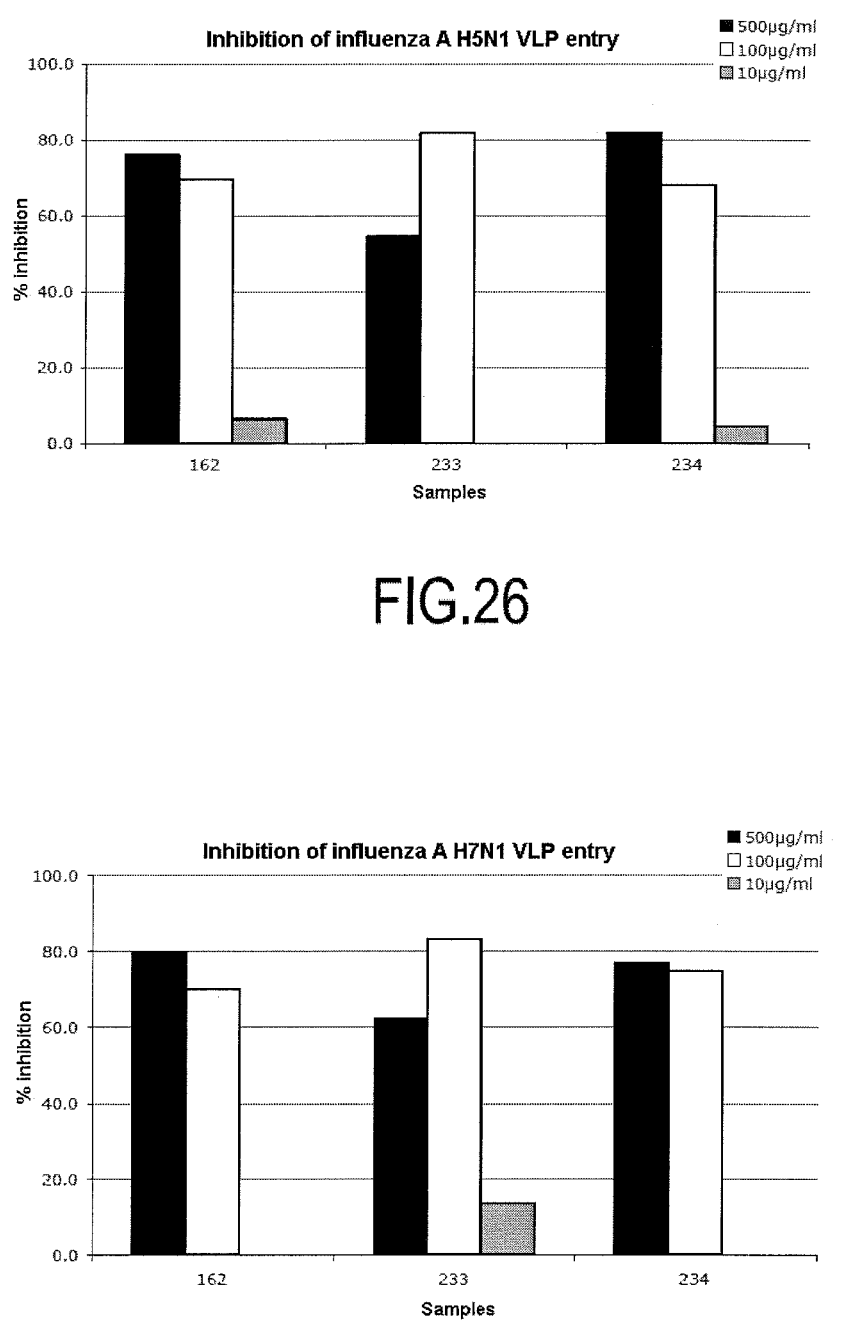

FIG. 26 presents the inhibitory activity of the sulfated heteroglycans 162, 233 and 234 tested on the entry of influenza A H5N1 VLPs, at concentrations of 10, 100 and 500 µg/ml.

FIG. 27 presents the inhibitory activity of the sulfated heteroglycans 162, 233 and 234 tested on the entry of influenza A H7N1 VLPs, at concentrations of 10, 100 and 500 µg/ml.

Figures 28, 29:
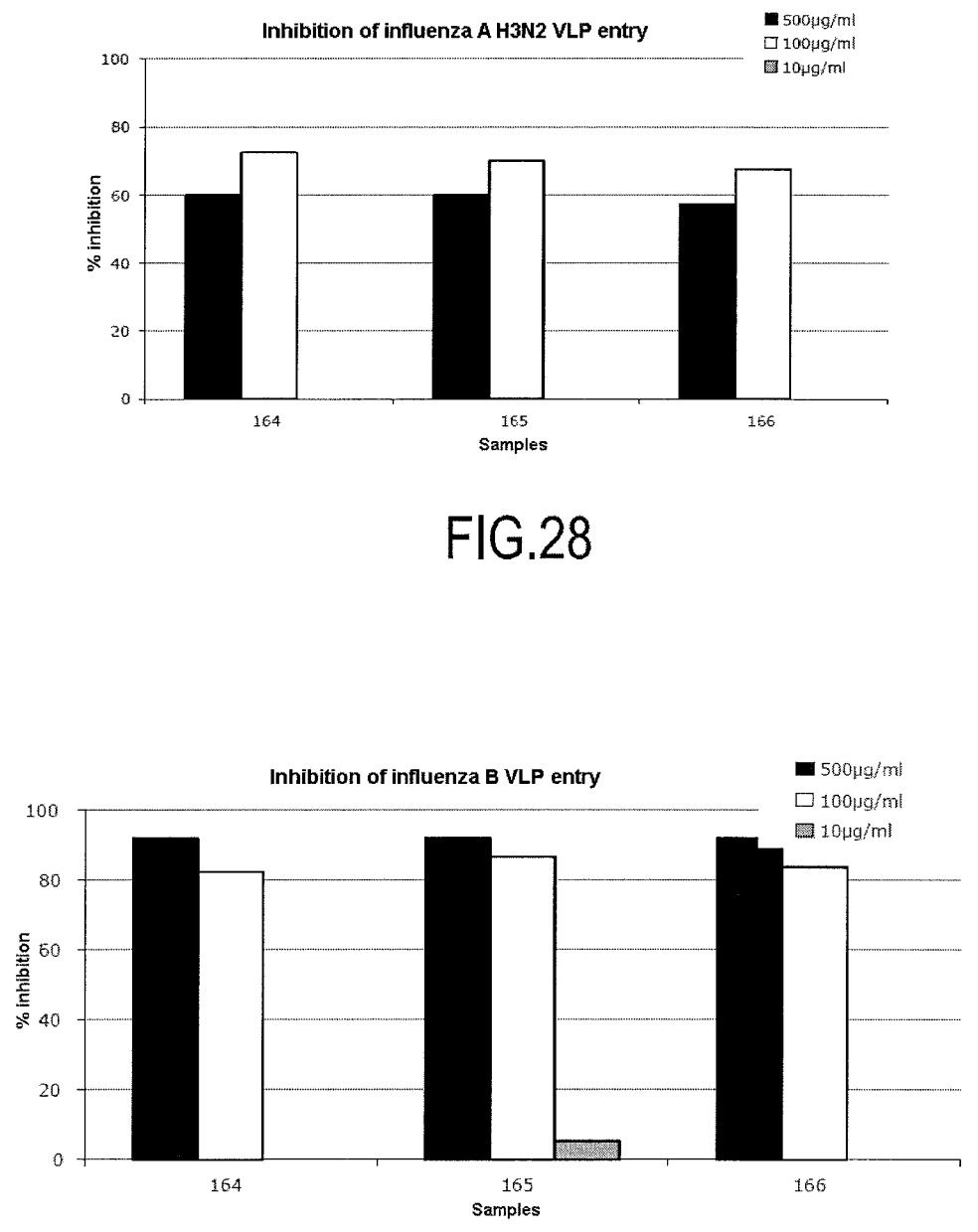

FIG. 28 presents the inhibitory activity of the carrageenans 164, 165 and 166 tested on the entry of influenza A H3N2 VLPs, at concentrations of 10, 100 and 500 µg/ml.

FIG. 29 presents the inhibitory activity of the carrageenans 164, 165 and 166 tested on the entry of influenza B VLPs, at concentrations of 10, 100 and 500 µg/ml.

FIG. 30 presents the inhibitory activity of the carrageenans 164, 165 and 166 tested on the entry of influenza A H5N1 VLPs, at concentrations of 10, 100 and 500 µg/ml.

FIG. 31 presents the inhibitory activity of the carrageenans 164, 165 and 166 tested on the entry of influenza A H7N1 VLPs, at concentrations of 10, 100 and 500 µg/ml.

FIG. 32 presents the effect of the treatments with the sulfated arabinogalactan polysaccharide 294 with the sulfated heteroglycan polysaccharide 295 and with the apiogalacturonan polysaccharide 296 on the survival of mice infected with the influenza H1N1 A/Puerto Rico/8/34 virus (25 MLD50).

Figure 33:
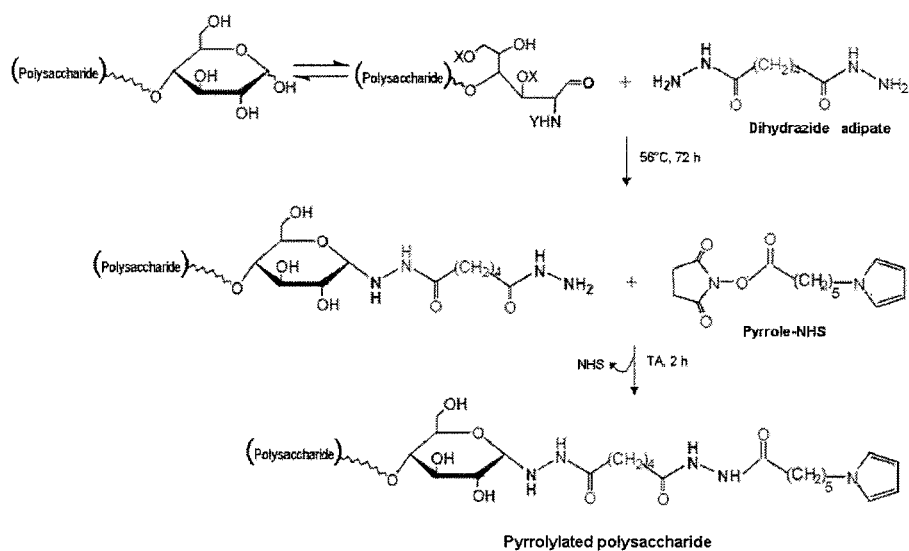

FIG. 33 summarizes the general principle of the coupling used in the examples for the preparation of pyrrolylated polysaccharides.

Figure 34:
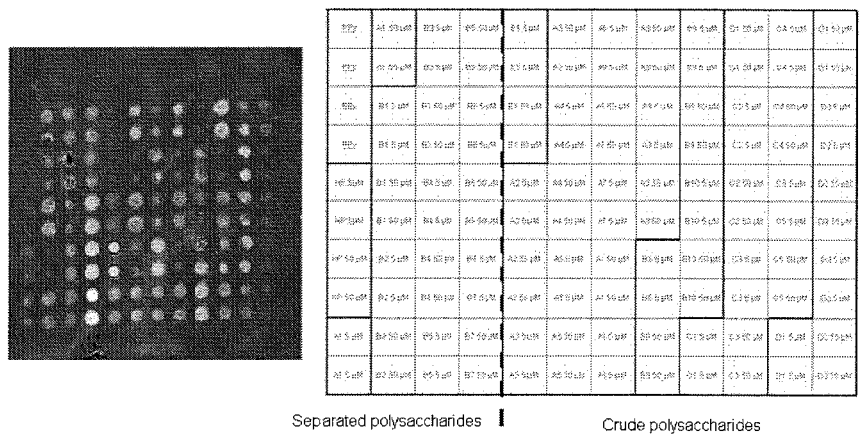

FIG. 34 is an illustration of the diagram for depositing the spots on the gold-plated surface of a prism used in the examples. In FIG. 34, the image on the left represents the prism seen in SPR imaging, during the injection of the HA1 (H1N1) protein at 600 nM.

Figure 35:
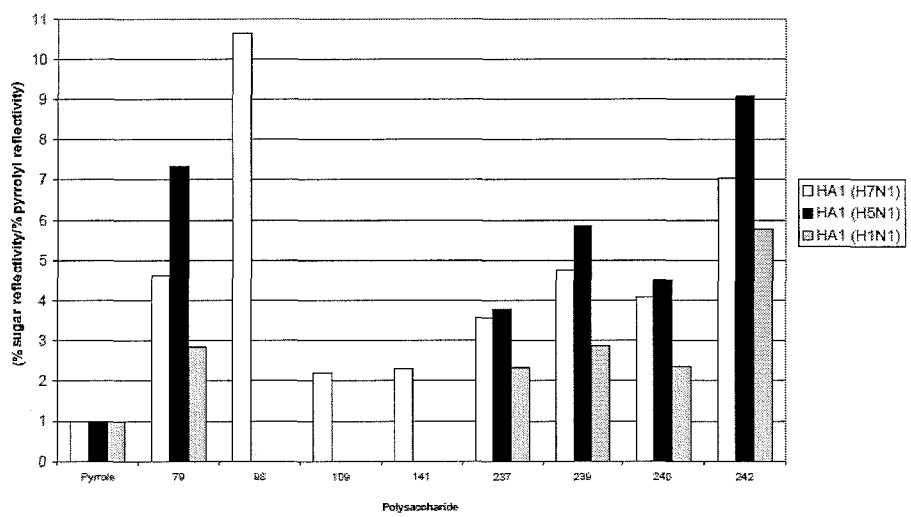

FIG. 35 presents the curves of interaction of the sulfated arabinogalactans tested in the examples with the HA1 protein.

Figure 36:
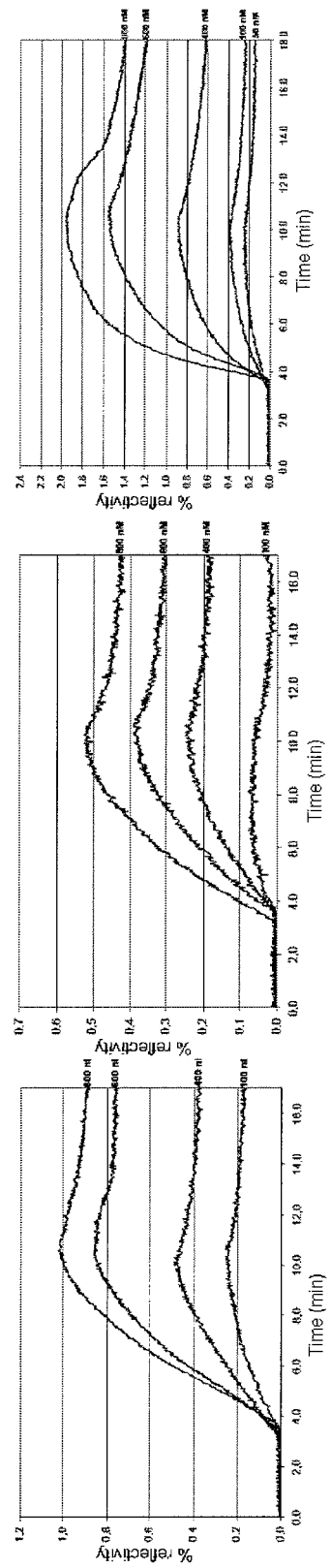

FIG. 36 presents the curves of association and dissociation between the arabinogalactan 79 and the HA1 of the three influenza viruses H7N1, H5N1 and H1N1, at various concentrations.

Figure 37:
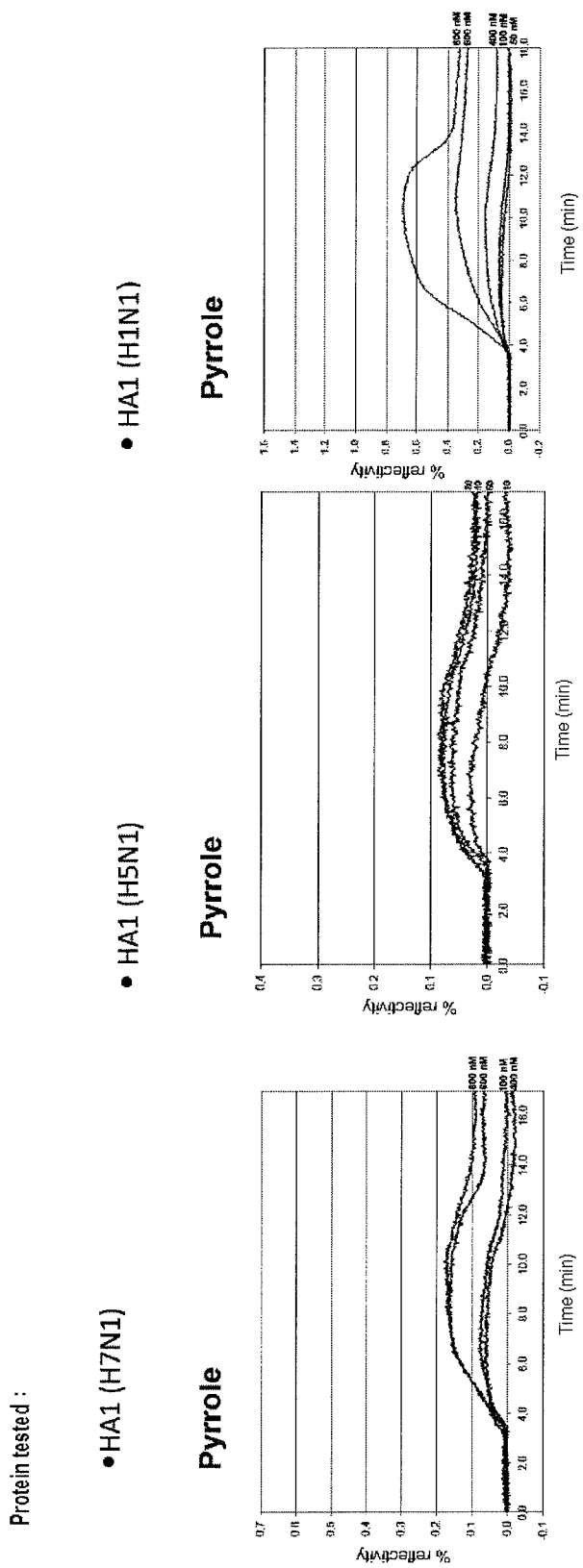

FIG. 37 presents the curves of association and dissociation between the pyrrole (negative control) and HA1 resulting from the three influenza viruses H7N1, H5N1 and H1N1, at various concentrations.

Figure 38:
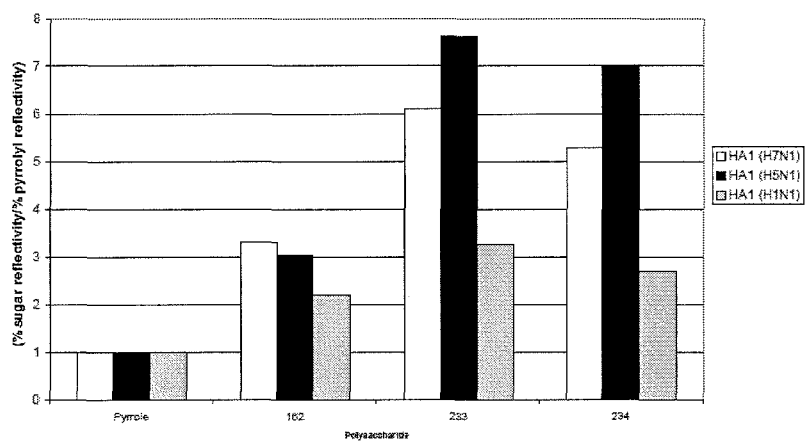

FIG. 38 presents the curves of interaction of the sulfated heteroglycans tested in the examples with the HA1 protein.

Figure 39:
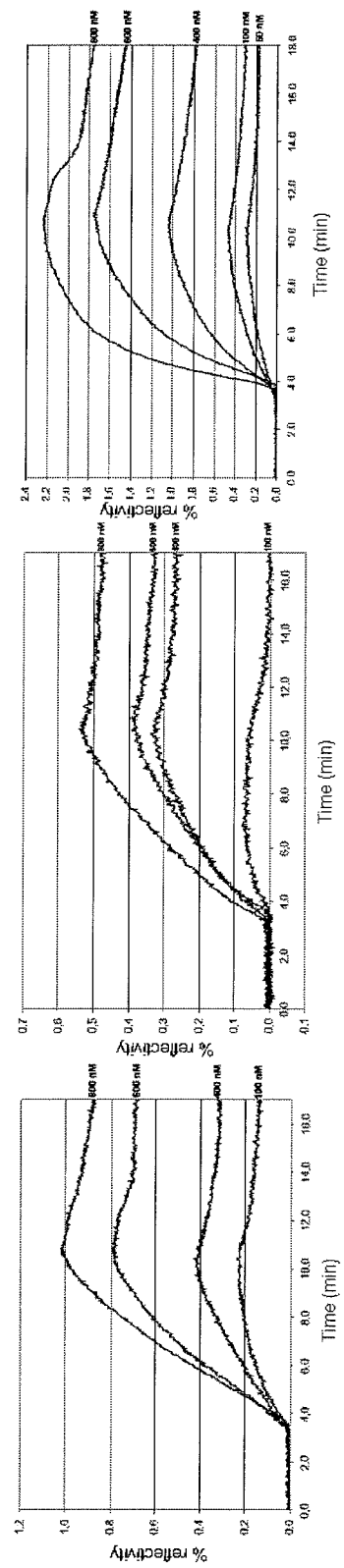

FIG. 39 presents the curves of association and dissociation between the sulfated heteroglycan 233 and the HA1 of the three influenza viruses H7N1, H5N1 and H1N1, at various concentrations.

FIG. 40 presents the curves of interaction of the carrageenans tested in the examples with the HA1 protein. The carrageenan polysaccharides, already described for their antiviral activity, serve as efficacy controls for the biological tests developed.

Figure 41:
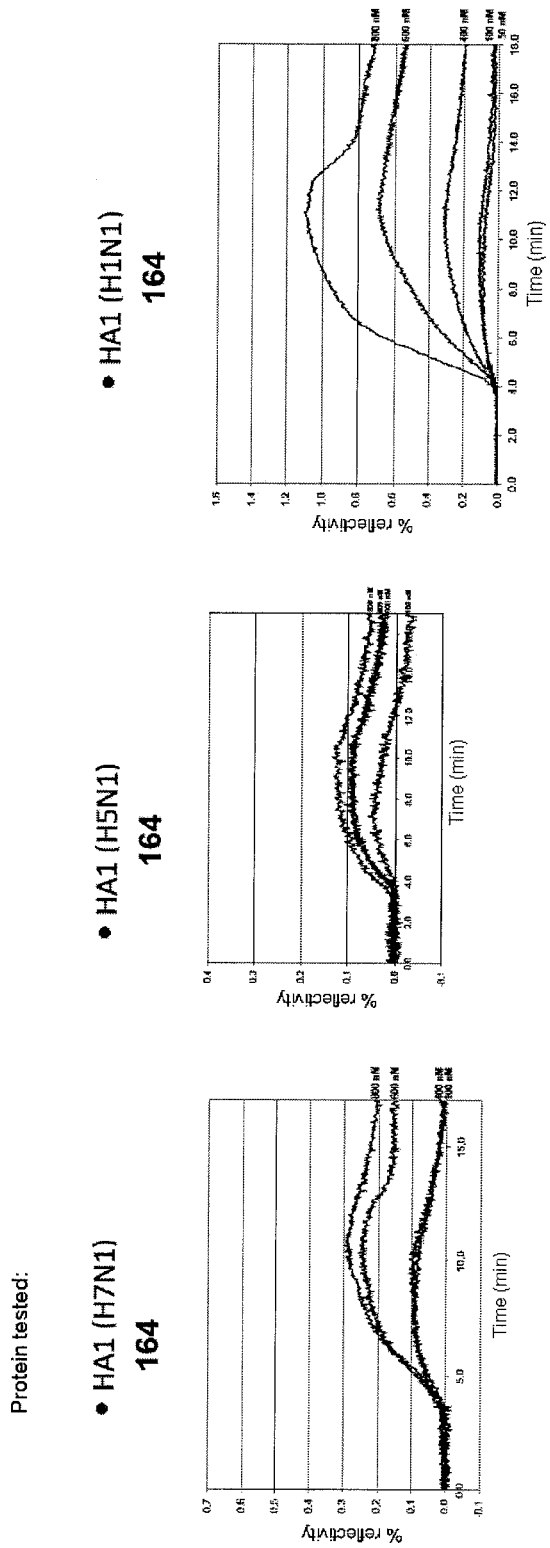

FIG. 41 presents the curves of association and dissociation between the carrageenan 164 and the HA1 of the three influenza viruses H7N1, H5N1 and H1N1, at various concentrations.

FIG. 42 summarizes the various infection modes carried out in the presence of 30 CCID50/50 µl of virus for a final arabinogalactan 152 concentration of 62.5 µg/ml.

Figure 43:
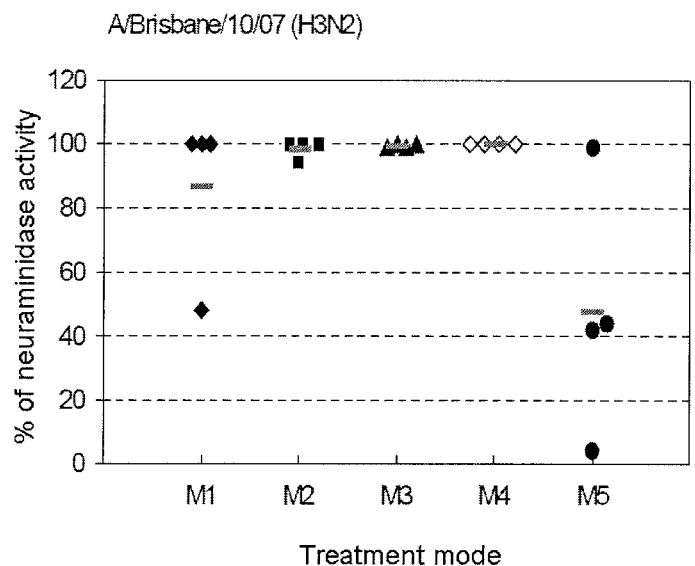
Figure 44:
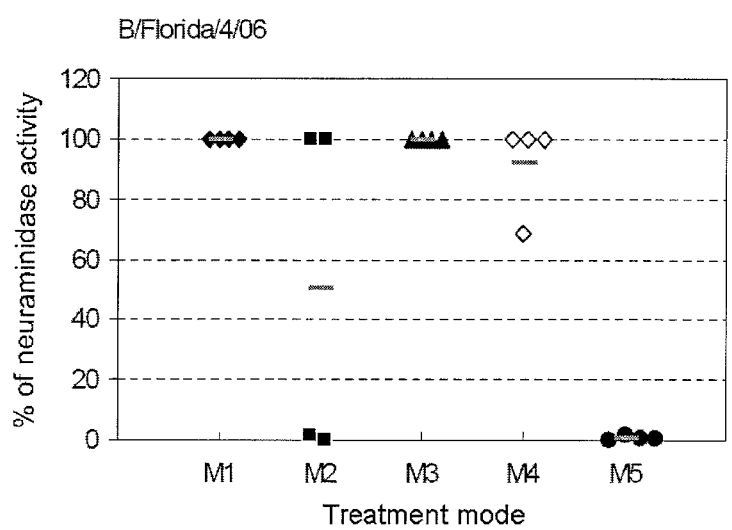

FIGS. 43 and 44 represent the results of viral replication inhibition obtained in the examples, according to the five infection modes for A/Brisbane/10/2007 H3N2 and B/Florida/4/06 viruses respectively.

1. Methods for Production and Physiochemical Characterization of the Polysaccharides Tested Sulfated Arabinogalactans Extracted from *Codium fragile*

The obtaining of the extracts of *Codium fragile* presented in the invention consists, in a first step, of the depigmentation of the ground algae with an organic solvent, in particular ethanol. The depigmented residue is then extracted, at ambient temperature, in an aqueous medium for a few hours to 24 h. The resulting extract can be improved by using polysaccharide purification methods, such as selective precipitation with organic solvents, for instance ethanol, and/or by ionic interaction, and/or dialysis by ultrafiltration.

The resulting extract has predominantly the described structure of sulfated arabinogalactan (Marina Ciancia et al. 2007—International Journal of Biological Macromolecules 41 (2007) 641-649), namely a linear chain of galactoses linked to one another via beta-1,3-glycosidic linkages. This main chain can have branches of arabinose or galactose units via alpha-1,6-glycosidic linkages. These units can have several arabinoses and/or galactoses linked to one another via 1,3- or 1,6-glycosidic linkages. The arabinoses or galactoses can have sulfations on secondary alcohol groups.

The monosaccharide composition of the extracts obtained in the context of this invention is confirmed by assaying monosaccharides using the HPAEC PAD chromatography technique following total acid hydrolysis. The extracts exhibit arabinose and galactose (3/7 to 1/1). The characteristic signals of the glycosidic linkages of the arabinogalactan are demonstrated by proton nucleomagnetic resonance. Assays of the sulfate groups using the barium chloride method make it possible to assess the degree of sulfation of the extracts of between 18% and 30% by weight. Size exclusion chromatography (SEC) of the polymers makes it possible to estimate the average molecular weight of the sulfated arabinogalactan polysaccharides present in the extracts. Said molecular weight, depending on the samples, is in the range of from approximately 3000 to approximately $1.1 \times 10^6$ g/mol.

Process for Obtaining the *Codium fragile* Extracts:

The various methods for obtaining the various samples tested are presented diagrammatically in FIG. 1.

The alga may be depigmented. 50 g of powdered *Codium fragile* can be depigmented by means of 4 successive washes with an organic solvent such as ethanol. Each wash consists in suspending the 50 g of algal powder in one liter of pure ethanol and stirring for 2 h at 400 rpm with a temperature of 20° C. After each wash, the extraction residue is isolated by filtration through Whatman paper. This operation is repeated three times. Following these depigmentation steps, the extraction residue is dried overnight in an incubator at 40° C.

The depigmentation residue can be extracted in an aqueous medium. The residue corresponding to the depigmented 50 g of *Codium fragile* is resuspended in 1 l of deionized water, and stirred for 16 h at 600 rpm and at ambient temperature. After 16 h, the soluble extract is isolated by centrifugation (7000 rpm, 4° C., 40 minutes approximately). This aqueous extract is called aqueous extract A.

The extracted sample No. 98 is obtained by desalification of the aqueous extract A by tangential ultrafiltration on a 10 kDa membrane. The desalification is obtained after diafiltration with the passing of 6 volumes of deionized water, i.e. 6 l. The ultrafiltration retentate corresponds to the sample No. 98.

The extracted sample No. 79 is obtained by means of a further step of refining the sample No. 98 by tangential ultrafiltration on a 0.2 µm membrane. This ultrafiltration is carried out at a concentration of 10 g/l with diafiltration in deionized water of 10 volumes. The fraction retained corresponds to the extracted sample No. 79.

The aqueous extract A can also be treated by tangential ultrafiltration on a 0.2 µm membrane. This ultrafiltration is carried out at a concentration of 10 g/l with a diafiltration in deionized water of 10 volumes. The fraction retained corresponds to the extracted sample No. 141.

The alga can be directly extracted with an aqueous solvent. 50 g of powdered *Codium fragile* are placed in solution in 1 l of deionized water with stirring at 400 rpm, at ambient temperature overnight. The soluble extract is isolated by centrifugation (8000 rpm, 4° C., 60 minutes). This aqueous extract is called aqueous extract B.

The extracted samples No. 109 and 238 are obtained by precipitation with an organic solvent, such as ethanol. For this, the aqueous extract B is precipitated with 50% v/v of pure ethanol. The precipitate is isolated by centrifugation (5000 rpm, 4° C., 10 minutes).

The extracted sample No 294 is obtained by means of a further step of refining the sample No. 109 or 238 by ionic interactions. This purification step by ionic interactions is carried out on an anion exchange support, in particular polysaccharide microbeads formed from crosslinked chitosan. In a first step, the sample No. 109 or 238 is placed in solution preferably at a pH of 4-5 by acidification, in particular with hydrochloric acid. The sample is then brought into contact with the ion exchange support, then rinsed with deionized water, which is preferentially acidified, in particular with hydrochloric acid, so as to reach a pH of 4-5. In a second step, the sugar of interest is released from the support with a basic buffer, in particular a bicarbonate/carbonate buffer, preferentially adjusted to a pH of approximately 10. The soluble fraction is isolated, preferentially by filtration. This fraction is then desalified, in particular by a precipitation with an organic solvent, such as ethanol. For this, the fraction is concentrated, preferentially to a concentration of from 1 to 10 g/l of polysaccharides, and then precipitated with 50% v/v of pure ethanol. The precipitate is isolated by centrifugation (5000 rpm, 4° C., 10 minutes) and then dried in an incubator. The resulting fraction is the sample No. 294.

The extracted sample No. 242 is obtained by means of a further step of refining the sample No. 109 or 238 by tangential ultrafiltration on a 0.2 µm membrane. This ultrafiltration is carried out at a concentration of 10 g/l with a diafiltration in deionized water of 10 volumes. The fraction retained corresponds to the extracted sample No. 242.

The extracted sample No. 152 is obtained by acid hydrolysis, in particular with hydrochloric acid, of the extracted samples No. 109 or 238, followed by molecular weight selection on two ultrafiltration membranes of 3 and 10 kDa. The weight selection is carried out by means of a first tangential ultrafiltration on a 10 kDa membrane carried out at 10 g/l with a diafiltration of 10 volumes with deionized water. The permeate is then passed through a 3 kDa membrane by tangential ultrafiltration, with a first phase of 10-fold concentration, followed by a diafiltration of 10 volumes with deionized water. The retentate of this second tangential ultrafiltration on a 3 kDa membrane constitutes the extracted sample No. 152.

The extracted samples No. 237 and 239 are obtained by treatment of the aqueous extract B with bentonite, followed by precipitation with ethanol. The aqueous extract B resulting from the extraction of 50 g of *Codium fragile* in 1 l of water is treated by adding 10 g of bentonite previously resuspended in 100 ml of deionized water. The solution is stirred, and then left to stand for approximately 1 h at ambient temperature. The soluble phase is isolated by centrifugation (8000 rpm, 4° C., 15 minutes). The isolated soluble phase is precipitated with an organic solvent, in particular with ethanol at a final concentration of 50% v/v. The precipitate is isolated by centrifugation (5000 rpm, 4° C., 10 minutes) and constitutes the extracted samples No. 237 and 239.

The extracted sample No. 240 is obtained by means of a further step of refining the sample No. 237 or 239 by tangential ultrafiltration on a 0.2 µm membrane. This ultrafiltration is carried out at a concentration of 10 g/l with a diafiltration in deionized water of 10 volumes. The fraction retained corresponds to the extracted sample No. 240.

Characterization of the Extracts of *Codium fragile*:

The extracts obtained have predominantly the described structure of sulfated arabinogalactan (Marina Ciancia et al. 2007—International Journal of Biological Macromolecules 41 (2007) 641-649), namely a linear chain of galactoses linked to one another via beta-1,3-glycosidic linkages. This main chain can have branches of arabinose or galactose units via alpha-1,6-glycosidic linkages. These units can have several arabinose and/or galactose units linked to one another via 1,3- or 1,6-glycosidic linkages. The arabinoses or galactoses can have sulfations on secondary alcohol groups.

It was possible to implement various methodologies for characterizing complex sugars in order to confirm the presence of the sulfated arabinogalactan in the extracts used for this invention:

Colorimetric assay of reducing sugars according to the DNS method after acid hydrolysis of the extract for 4 h at 100° C. with 2N TFA.

Colorimetric assay of proteins according to the Lowry-Folin method.

Tubidimetric assay of sulfates according to the barium chloride method.

Monosaccharide profile according to the HPAEC-PAD method after acid hydrolysis of the extract for 4 h at 100° C. with TFA.

Proton nucleomagnetic resonance spectrum.

Estimation of the molecular weight range of the polymers by SEC.

Colorimetric Assays

| Extracted sample | Total sugars (1) | Proteins (2) | Sulfates (3) |
|---|---|---|---|
| 79 | 45 | 5 | 28 |
| 98 | 47 | 10 | 24 |
| 109 | 50 | 8 | 23 |
| 141 | 38 | 7 | 18 |
| 152 | 42 | 8 | 19 |
| 237 | 41 | 2 | 30 |
| 238 | 34 | 9 | 26 |
| 239 | 38 | 2 | 28 |
| 240 | 41 | 2 | 26 |
| 242 | 46 | 5 | 26 |
| 295 | 44 | 6 | 26 |

(1) Total sugars expressed as % w/w eq Gal
(2) Proteins expressed as % w/w eq BSA
(3) Sulfates expressed as % $SO_3^-$ w/w Monosaccharide Profile

| Extracted sample | Monosaccharides | | | | | | | | |
| --- | --- | --- | --- | --- | --- | --- | --- | --- | --- |
| | Fuc | Rha | Ara | Gal | Glc | Man | Xyl | Ac Gal | Ac Glc |
| 79 | 1 | 0 | 17 | 18 | 0 | 1 | 1 | 0 | 0 |
| 98 | 1 | 0 | 15 | 16 | 1 | 2 | 1 | 0 | 0 |
| 109 | | | | | | | | | |
| 141 | 1 | 0 | 13 | 13 | 1 | 1 | 0 | 0 | 0 |
| 152 | 2 | 0 | 37 | 33 | 9 | 4 | 2 | 0 | 0 |
| 237 | 0 | 0 | 12 | 7 | 1 | 1 | 0 | 0 | 0 |
| 238 | 0 | 0 | 15 | 11 | 2 | 1 | 1 | 0 | 0 |
| 239 | 1 | 0 | 19 | 10 | 2 | 2 | 0 | 0 | 0 |
| 240 | 1 | 0 | 24 | 13 | 0 | 0 | 1 | 0 | 0 |
| 242 | 1 | 0 | 22 | 14 | 0 | 1 | 1 | 0 | 0 |
| 295 | 1 | 0 | 31 | 48 | 1 | 1 | 2 | 1 | 2 |

Molecular Weight of the Polysaccharides

| Extracted sample | Estimation by SEC |
| --- | --- |
| 98 | 900 000 g/mol |
| 109 | 600 000 g/mol |
| 141 | 400 000 g/mol |
| 152 | 3000 to 10 000 g/mol |
| 237 | 50 000 g/mol |
| 238 | 700 000 g/mol |
| 239 | 1 100 000 g/mol |
| 240 | 950 000 g/mol |
| 242 | 1 100 000 g/mol |

Proton NMR

The signals observed correspond to the characteristic signals of the described structures of sulfated arabinogalactans.
Apiogalacturonan of Zostera marina:

The obtaining of the extracts of Zostera marina presented in the invention consists, in a first step, of the depigmentation of the plant with an organic solvent, in particular ethanol. The depigmented residue is then hot-extracted in an aqueous medium for a few hours to 24 h. The extracted residue undergoes a second extraction in an acidic medium, in particular in a TFA medium. The extraction polysaccharide is obtained by precipitation according to the pH of the filtrate previously obtained. This polysaccharide can be improved using polysaccharide purification methods such as selective precipitation with organic solvents such as ethanol, and/or dialysis by ultrafiltration.

The resulting extract has predominantly the described structure of apiogalacturonan (Véronique Brudieux—2007 Doctorate thesis—Limoges University—Extraction, enzymatic modification and chemical characterization of novel pectic structures. Application of the structure/activity relationship to dermocosmetics.), namely a linear chain of galacturonic acids linked to one another via alpha-1,4-glycosidic linkages. This main chain can have, as branches, apiose units linked via beta-1,2-glycosidic linkages. These units can have several apioses linked to one another via beta-1,5-glycosidic linkages.

The monosaccharide composition of the extracts obtained in the context of this invention is confirmed by assaying monosaccharides using the HPAEC PAD chromatography technique following total acid hydrolysis and by the technique of gas chromatography after monosaccharide derivation by acetylation. The extracts exhibit galacturonic acid and apiose. The characteristic signals of the glycosidic linkages of the apiogalacturonan are demonstrated by proton nucleomagnetic resonance, in particular the alpha-1,4 galacturonic acid chain after partial acid hydrolysis of apioses. Assays of sulfate groups using the barium chloride method make it possible to evaluate the degree of sulfation of the extracts at between 4% and 12% by weight. SEC of the polymers makes it possible to estimate the average molecular weight of the sulfated arabinogalactan polysaccharides present in the extracts, which ranges from 50 000 to 700 000 g/mol.

Process for Obtaining the Extracts of Zostera marina

The various methods for obtaining the various samples tested are presented diagrammatically in FIG. 3.

The first method makes it possible to obtain the extracted sample No. 138. The marine plant Zostera marina, in powder form, is washed with water. 40 g of Zostera marina powder are placed in solution in 1 l of deionized water for 5 hours approximately at 95° C. with stirring at 500 rpm. The washing residue is isolated by centrifugation (8000 rpm, 4° C., 20 minutes).

The pellet obtained is then extracted in an acidic medium, for example with TFA. The washing residue is placed in solution again in 1 l of 0.5N TFA, stirred at 500 rpm for 2 hours approximately at 25° C. The soluble fraction is isolated by centrifugation (8000 rpm, 4° C., 30 minutes). The soluble fraction thus isolated is neutralized at pH 7.5, and a precipitate appears. The precipitate is isolated by centrifugation (8000 rpm, 4° C., 30 minutes). This precipitate is placed in solution again with 1 l of deionized water. This solution is then precipitated with ethanol, placed beforehand at −20° C., to 60% v/v final concentration. The precipitate formed is isolated by centrifugation (7000 rpm, 4° C., 10 minutes). The precipitate is placed in solution again at 10 g/l in order to be salified by tangential ultrafiltration on a 650 Da membrane. A diafiltration of 10 volumes is carried out with deionized water. The retentate obtained is lyophilized to give the extracted sample No. 138.

The pellet obtained during the first extraction with hot water can also be extracted in an acidic medium with hydrochloric acid. The washing residue is placed in solution again in 1 l of 0.5N HCl, stirred at 500 rpm for 2 hours approximately at 25° C. The soluble fraction is isolated by centrifugation (8000 rpm, 4° C., 30 minutes). The soluble fraction that is isolated is neutralized at pH 7.5, and a precipitate appears. The precipitate is isolated by centrifugation (8000 rpm, 4° C., 30 minutes). This precipitate is placed in solution again with 1 l of deionized water. This solution is then precipitated with ethanol placed beforehand at −20° C., to 60% v/v final concentration. The precipitate formed is isolated by centrifugation (7000 rpm, 4° C., 10 minutes). The precipitate dried in an incubator gives the extracted sample No. 296.

The second method concerns an extraction of Zostera marina with oxalate after depigmentation with an organic solvent such as ethanol. 50 g of powdered Zostera marina are suspended in 1 l of pure ethanol. The mixture is brought to 78° C. with stirring at 500 rpm for 5 hours approximately. The depigmentation residue is isolated by filtration on a 20-25 µm Büchner filter and dried in an incubator at 40° C. overnight. The depigmented marine plant is then placed in solution again in 1 l of 1% ammonium oxalate with stirring at 750 rpm at 70° C. for 2 hours approximately. The soluble extract is isolated by centrifugation (8000 rpm, 4° C., 30 minutes). The extracted fraction can be desalified by tangential ultrafiltration on 10 kDa membranes. The diafiltraton of approximately 10 volumes is carried out with deionized water. The retentate is lyophilized to give the extracted sample No. 158.

The third method concerns an extraction of Zostera marina with 3% sodium carbonate after depigmentation with an organic solvent such as ethanol. 50 g of powdered Zostera

*marina* are suspended in 1 l of pure ethanol. The mixture is brought to 78° C. with stirring at 500 rpm for approximately 5 hours. The depigmentation residue is isolated by filtration on a 20-25 µm Büchner filter and dried in an incubator at 40° C. overnight. The depigmented marine plant is then placed in solution again in 1 l of 3% sodium carbonate with stirring at 500 rpm at 70° C. for approximately 2 hours. The soluble extract is isolated by centrifugation (8000 rpm, 4° C., 30 minutes), and then neutralized with hydrochloric acid. The product thus isolated is precipitated with ethanol, placed beforehand at −20° C., to 50% v/v final concentration. The precipitate is isolated by centrifugation (6000 rpm, 4° C., 5 minutes). The precipitate can be washed several times, for example three times, with pure ethanol. It is then dried in an incubator at 40° C. overnight approximately. The dried precipitate can then be desalified by tangential ultrafiltration on 10 kDa membranes. A diafiltration of approximately 10 volumes is carried out with deionized water. The retentate is lyophilized to give the extracted sample No. 160. The retentate can also be precipitated with an organic solvent such as ethanol, placed beforehand at −20° C., to 50% v/v final concentration. The precipitate is isolated by centrifugation at 6000 rpm at 4° C. for approximately 5 minutes. The precipitate can be washed several times, for example three times, with pure ethanol. It is then dried in an incubator at 40° C. overnight approximately. The dried precipitate constitutes the extracted sample No. 161.

Characterization of the Extracts of *Zostera marina*:

The resulting extracts have predominantly the described structure of apiogalacturonan (Véronique Brudieux—2007 doctorate thesis—Limoges University—Extraction, enzymatic modification and chemical characterization of novel pectic structures. Application of the structure/activity relationship to dermocosmetics), namely a linear chain of galacturonic acids linked to one another via alpha-1,4-glycosidic linkages. This main chain can have apiose units linked via beta-1,2-glycosidic linkages. These units can have several apioses linked to one another via beta-1,5-glycosidic linkages.

It was possible to implement various methodologies for characterizing complex sugars in order to confirm the presence of apiogalacturonan in the extracts used for this invention:

Colorimetric assay of reducing sugars according to the DNS method after acid hydrolysis of the extract for 4 h at 100° C. with 2N TFA or 2N $H_2SO_4$.

Colorimetric assay of proteins according to the Lowry-Folin method.

Turbidimetric assay of sulfates according to the barium chloride method.

Monosaccharide profile according to the HPAEC-PAD method after acid hydrolysis of the extract for 4 h at 100° C. with 2N TFA or 2N $H_2SO_4$.

Identification of the apiose monosaccharide using the technique of gas chromatography after monosaccharide derivation by acetylation.

Proton nucleomagnetic resonance spectrum.

Estimation of the molecular weight range of the polymers by SEC.

Colorimetric Assays

| Extracted sample | Total sugars (1) | Proteins (2) | Sulfates (3) |
|---|---|---|---|
| 158 | 44 | 4 | 5 |
| 160 | 19 | 26 | 4 |
| 161 | 31 | 16 | 0 |
| 138 | 58 | 2 | 0 |
| 294 | 52 | 1 | 0 |

(4) Total sugars expressed as % w/w eq Gal
(5) Proteins expressed as % w/w eq BSA
(6) Sulfates expressed as % $SO_3^-$ w/w Monosaccharide Profile

| Extracted sample | Monosaccharides | | | | | | | | |
|---|---|---|---|---|---|---|---|---|---|
| | Fuc | Gal | Glc | Man | Apiose | Ac Gal | Ac Gul | Ac Glc | Ac Man |
| 158 | 3 | 2 | 0 | 1 | 3 | 5 | 14 | 3 | 33 |
| 160 | 3 | 1 | 1 | 1 | 3 | 3 | 12 | 3 | 28 |
| 161 | 2 | 1 | 0 | 0 | 3 | 4 | 18 | 2 | 37 |
| 138 | 0 | 1 | 0 | 0 | 18 | 18 | 0 | 1 | 0 |
| 294 | 2 | 1 | 1 | 0 | 29 | 62 | 0 | 1 | 0 |

Molecular Weight of the Polysaccharides

| Extracted sample | Estimation by SEC |
|---|---|
| 158 | 90 000-400 000 g/mol |
| 160 | 150 000-400 000 g/mol |
| 161 | 90 000-200 000 g/mol |
| 138 | 490 000 g/mol |

Proton NMR

The proton NMR spectra of the samples No. 158, 160 and 161 reveal the characteristic structure of apiogalacturonan with the presence of the two apiose monosaccharides and galacturonic acid in equivalent amounts. The presence of mannuronic acid and of guluronic acid suggests the presence of alginates.

For the extracted sample No. 138, the proton NMR spectra demonstrate the characteristic signals of apiose. After partial hydrolysis with TFA, the proton NMR spectra demonstrate the characteristic signals of the main chain of alpha-1,4-linked galacturonic acids. This extract exhibits the apiogalacturonan polysaccharide.

Sulfated Heteroglycan Extracted from *Caulerpa racemosa*:

The obtaining of the extracts of *Caulerpa racemosa* presented in the invention consists, in a first step, of the depigmentation of the ground algae with an organic solvent, in particular ethanol. The depigmented residue is then hot-extracted in an aqueous medium for a few hours to 24 h. The resulting extract can be improved using polysaccharide purification methods such as selective precipitation with organic solvents such as ethanol, and/or by ionic interaction, and/or dialysis by ultrafiltration.

The resulting extract has predominantly the described structure of sulfated heteroglycan (Chattopadhyay Kausik et al. 2006—Carbohydrate polymers 2007, vol. 68, No. 3, pp. 407-415), namely alpha-1,3-linked and terminally-linked galactose, 1,4-linked xyloses and 1,4-linked arabinoses. The galactoses can have sulfations in the C6 position and the arabinoses can have sulfations in the C3 position.

The monosaccharide composition of the extracts obtained in the context of this invention is confirmed by assaying monosaccharides using the HPAEC PAD chromatography technique following total acid hydrolysis. The extracts exhibit arabinose, galactose and xylose (10/10/0.5 to 13/13/1). The characteristic signals of the glycosidic linkages of xyloarabinogalactan are demonstrated by proton nucleomagnetic resonance. Assays of sulfate groups by the barium chloride method make it possible to evaluate the degree of sulfation of the extracts at between 22% and 13% by weight. SEC of the polymers makes it possible to estimate the average molecular weight of the sulfated arabinogalactan polysaccharides present in the extracts at approximately $10^6$ g/mol.

Process for Obtaining the Extracts of *Caulerpa racemosa*

The various methods for obtaining the various samples tested are presented diagrammatically in FIG. 2.

An aqueous-phase extraction is carried out on the powdered alga. 70 g of powdered *Caulerpa racemosa* are suspended in 1 l of deionized water, and stirred overnight, with stirring at 650 rpm, at 80° C. The soluble extract is then isolated by centrifugation (8000 rpm, 4° C., 30 minutes). This extract is called the aqueous extract.

The extracted samples No. 162 and 234 are obtained by cold-precipitation of the aqueous extract with an organic solvent, such as ethanol. For this, the aqueous extract is precipitated with 50% v/v of pure ethanol placed beforehand at −20° C. The precipitate is isolated by centrifugation (4000 rpm, 4° C., 10 minutes). The precipitate can be washed several times, for example three times, with pure ethanol. It is then dried in an incubator at 40° C. overnight.

The extracted sample No. 295 is obtained by means of a further step of refining the sample No. 162 or 234 by ionic interactions. This step of purification by ionic interactions is carried out on an anion exchange support, in particular polysaccharide microbeads formed from crosslinked chitosan. In a first step, the sample No. 162 or 234 is placed in solution preferentially at a pH of 4-5 by acidification, in particular with hydrochloric acid. The sample is then brought into contact with the ion exchange support, then rinsed with deionized water, which is preferentially acidified, in particular with hydrochloric acid, so as to reach a pH of 4-5. In a second step, the sugar of interest is released from the support with a basic buffer, in particular a bicarbonate/carbonate buffer, preferentially adjusted to a pH of approximately 10. The soluble fraction is isolated, preferentially by filtration. This fraction is then desalified, in particular by precipitation with an organic solvent, such as ethanol. For this, the fraction is concentrated, preferably to a polysaccharide concentration of from 1 to 10 g/l, and then precipitated with 50% v/v of pure ethanol. The precipitate is isolated by centrifugation (5000 rpm, 4° C., 10 minutes) and then dried in an incubator. The resulting fraction is the sample No. 295.

The aqueous extract can also be treated with bentonite in order to improve its purification, and then precipitated with an organic solvent, in particular ethanol. The aqueous extract resulting from the extraction of 70 g of *Caulerpa racemosa* in 1 l of water is treated by adding 6.5 g of bentonite suspended beforehand in 65 ml of deionized water. The solution is stirred, and then left to stand for 1 h approximately at ambient temperature. The soluble phase is isolated by centrifugation (8000 rpm, 4° C., 15 minutes). The product thus isolated is precipitated with ethanol, placed beforehand at −20° C., to 50% v/v final concentration. The precipitate is isolated by centrifugation (5000 rpm, 4° C., 10 minutes). The precipitate can be washed several times, for example three times, with pure ethanol. It is then dried in an incubator at 40° C. overnight. The precipitation residue constitutes the extracted sample No. 233.

Characterization of the Extracts of *Caulerpa racemosa*:

The resulting extracts have predominantly the described structure of sulfated heteroglycan (Chattopadhyay Kausik et al. 2006—Carbohydrate polymers 2007, vol. 68, No. 3, pp. 407-415), namely alpha-1,3-linked and terminally-linked galactoses, 1,4-linked xyloses and 1,4-linked arabinoses. The galactoses can have sulfations in the C6 position and the arabinoses can have sulfations in the C3 position.

It was possible to implement various methodologies for characterizing complex sugars in order to confirm the presence of sulfated heteroglycan in the extracts used for this invention:

Colorimetric assay of reducing sugars according to the DNS method after acid hydrolysis of the extract for 4 h at 100° C. with 2N TFA.

Colorimetric assay of proteins according to the Lowry-Folin method.

Turbidimetric assay of sulfates according to the barium chloride method.

Monosaccharide profile according to the HPAEC-PAD method after acid hydrolysis of the extract for 4 h at 100° C. with TFA.

Proton nucleomagnetic resonance spectrum.

Estimation of the molecular weight range of the polymers by SEC.

Colorimetric Assays

| Extracted sample | Total sugars (1) | Proteins (2) | Sulfates (3) |
|---|---|---|---|
| 162 | 48 | 4 | 13 |
| 233 | 50 | 3 | 22 |
| 234 | 50 | 5 | 21 |
| 296 | 52 | 2 | 23 |

(1) Total sugars expressed as % w/w eq Glc
(2) Proteins expressed as % w/w eq BSA
(3) Sulfates expressed as % $SO_3^-$ w/w Monosaccharide Profile

| Extracted sample | Monosaccharides | | | | | | | | |
|---|---|---|---|---|---|---|---|---|---|
| | Fuc | Rha | Ara | Gal | Glc | Man | Xyl | Ac Gal | Ac Glc |
| 162 | 0 | 0 | 11 | 13 | 17 | 10 | 1 | 0 | 0 |
| 233 | 0 | 0 | 13 | 13 | 14 | 3 | 1 | 0 | 0 |
| 234 | 0 | 0 | 11 | 13 | 12 | 9 | 1 | 0 | 0 |
| 296 | 0 | 0 | 11 | 28 | 4 | 14 | 1 | 0 | 0 |

Molecular Weight of the Polysaccharides

| Extracted sample | Estimation by SEC |
|---|---|
| 162 | $10^6$ g/mol |

Proton NMR

The signals observed correspond to the characteristic signals of the described structures of sulfated heteroglycans.

Ulvans—Extracts of *Ulva armoricana*

Process for Obtaining the Extracts of *Ulva armoricana*

The various methods for obtaining the various samples tested are presented diagrammatically in FIG. 4.

The ground *Ulva armoricana* alga is treated by aqueous-phase extraction. 70 g of *Ulva armoricana* are suspended in one liter of deionized water, at 95° C. for approximately 12 hours with stirring at 850 rpm. The soluble extract is isolated by centrifugation (8000 rpm, 4° C., 45 minutes). The product thus isolated is precipitated with ethanol, placed beforehand at −20° C., to 60% v/v final concentration. The precipitate is isolated by centrifugation (4000 rpm, 4° C., 5 minutes). The precipitate can be washed several times, for example three times, with pure ethanol. It is then dried in an incubator at 40° C. overnight. The precipitated extract is then purified on tangential ultrafiltration membranes. In a first step, the precipitated extract is placed in solution again at 5 g/l and diafiltered with 10 volumes of deionized water on a 300 kDa membrane. The permeate of this ultrafiltration is 10-fold concentrated on a second tangential ultrafiltration membrane of 100 kDa, and then diafiltered with 10 volumes of deionized water. The retentate of this second ultrafiltration is lyophilized to give the extracted sample No. 244. The permeate is lyophilized, after concentration, to give the extracted sample No. 245.

Characterization of the Extracts of Ulva armoricana:

The resulting extract has predominantly the described structure of ulvan (Marc Lahaye, Carbohydrate Research 1998), namely a chain formed from units among the following four units:

Ulvanobiuric 3-sulfate type A acid: β(1,4)-D-GlcA-α (1,4)-L-Rha 3 sulfate

Ulvanobiuric 3-sulfate type B acid: β(1,4)-L-IdoA-α (1,4)-L-Rha 3 sulfate

Ulvanobiose 3-sulfate acid: β(1,4)-D-Xyl-α (1,4)-L-Rha 3 sulfate

Ulvanobiose 2', 3 disulfate acid: β(1,4)-D-Xyl 2-sulfate-α (1,4)-L-Rha 3 sulfate.

It was possible to implement various methodologies for characterizing complex sugars in order to confirm the presence of sulfated ulvan in the extracts used for this invention:

Colorimetric assay of reducing sugars according to the DNS method after acid hydrolysis of the extract for 4 h at 100° C. with 2N TFA.

Colorimetric assay of proteins according to the Lowry-Folin method.

Turbidimetric assay of sulfates according to the barium chloride method.

Monosaccharide profile according to the HPAEC-PAD method after acid hydrolysis of the extract for 4 h at 100° C. with TFA.

Colorimetric Assays

| Extracted sample | Total sugars (1) | Proteins (2) | Sulfates (3) |
| --- | --- | --- | --- |
| 244 | 36 | 1 | 17 |
| 245 | 23 | 14 | 5 |

(1) Total sugars expressed as % w/w eq Gal
(2) Proteins expressed as % w/w eq BSA
(3) Sulfates expressed as % $SO_3^-$ w/w Monosaccharide Profile

| Extracted sample | Monosaccharides | | | | | |
| --- | --- | --- | --- | --- | --- | --- |
|  | Rha | Xyl | Glc | Ac Gal | Ac Glu | Ac Idu |
| 244 | 28 | 3 | 5 | 2 | 10 | 9 |
| 245 | 5 | 2 | 14 | 0 | 2 | 1 |

Carrageenan—Extracts of *Agardhiella tenera*

Process for Obtaining the Extracts of *Agardhiella tenera*

The various methods for obtaining the various samples tested are presented diagrammatically in FIG. 5.

The ground *Agardhiella tenera* alga is treated by aqueous-phase extraction after depigmentation with an organic solvent such as ethanol. 200 g of powdered *Agardhiella tenera* are suspended in 1 l of pure ethanol. The mixture is brought to 78° C. with stirring at 500 rpm for approximately 3 hours. The depigmentation residue is isolated by filtration on a 20-25 μm Büchner filter and dried in an incubator at 40° C. overnight. The alga thus depigmented is then placed in solution again in 10 liters of deionized water, at 37° C. for approximately 6 hours with stirring at 850 rpm. The soluble extract is isolated by centrifugation (8000 rpm, 30° C., 30 minutes). The product thus isolated is precipitated with ethanol, placed beforehand at −20° C., to 67% v/v final concentration. The precipitate is isolated by centrifugation (4000 rpm, 4° C., 5 minutes). The precipitate can be washed several times, for example three times, with pure ethanol. It is then dried in an incubator at 40° C., forming the extracted sample No. 164. The soluble part resulting from the first precipitation step is taken up with addition of ethanol at −20° C. so as to reach a final concentration of ethanol of 83% v/v. The precipitate is isolated by centrifugation (4000 rpm, 4° C., 5 minutes). The precipitate can be washed several times, for example three times, with pure ethanol. It is then dried in an incubator at 40° C., forming the extracted sample No. 165. Ethanol at −20° C. is added to the soluble part resulting from the second precipitation step, so as to reach a final concentration of ethanol at 92% v/v. The precipitate can be washed several times, for example three times, with pure ethanol. It is then dried in an incubator at 40° C., forming the extracted sample No. 166.

Characterization of the Extracts of *Agardhiella tenera*:

These resulting extracts have predominantly the described structure of carrageenan.

It was possible to implement various methodologies for characterizing complex sugars in order to confirm the presence of carrageenans in the extracts used for this invention:

Colorimetric assay of reducing sugars according to the DNS method after acid hydrolysis of the extract for 4 h at 100° C. with 2N TFA.

Colorimetric assay of proteins according to the Lowry-Folin method.

Turbidimetric assay of sulfates according to the barium chloride method.

Proton nucleomagnetic resonance spectrum.

Estimation of the molecular weight range of the polymers by SEC.

Colorimetric Assays

| Extracted Sample | Total sugars (1) | Proteins (2) | Sulfates (3) |
| --- | --- | --- | --- |
| 164 | 46 | 2 | 25 |
| 165 | 42 | 2 | 25 |
| 166 | 42 | 2 | 26 |

(1) Total sugars expressed as % w/w eq Gal
(2) Proteins expressed as % w/w eq BSA
(3) Sulfates expressed as % $SO_3^-$ w/w Molecular Weight of the Polysaccharides

| Extracted Sample | Estimation by SEC |
| --- | --- |
| 164 | 500 000 g/mol |
| 165 | 550 000 g/mol |
| 166 | 490 000 g/mol |

Proton NMR

The proton NMR spectra demonstrate the characteristic signals of the carrageenan structures.

2. Activities a. Neutralization of Influenza Virus Replication

The identification of active samples is based on the evaluation of the capacity of molecules to block viral replication of the influenza virus on a cell system permissive to the latter. The evaluation was carried out with respect to type A and B influenza viruses, capable of inducing epidemics in the human population.

i). Procedure

The A/Brisbane/10/2007 H3N2, and B/Florida/4/06 viruses were used in the neutralization tests. These viruses represent antigenically the circulating strains of the 2008-2009 winter seasons for the southern and northern hemisphere. They were selected to be part of the vaccine composition of the corresponding winters.

Three sample concentrations were prepared in an infection medium (250 µg/ml; 25 µg/ml; 2.5 µg/ml). Each concentration is brought into contact with an equal volume of a standardized amount of virus. This mixture is deposited, at a rate of 4 wells per concentration, in 96-well plates coated with MDCK cells. Negative controls are carried out in order to verify the absence of cytopathic effect of uninfected MDCK cells. A control of the amount of virus used in the test is also deposited. After 48 hours of incubation, the % neutralization is determined by demonstrating the virus in the culture supernatant using an enzymatic test. In this assay, the viral neuraminidase hydrolyzes its substrate (2'-(4-methylumbelliferyl)-α-D-N-acetylneuraminic acid) and releases sialic acid and a fluorescent molecule, 4-methylumbelliferone. The amount of 4-methylumbelliferone released is determined by fluorimetric measurement. The amount demonstrated is referred to the amount of the positive control.

ii). Results

Six families of sugar were tested below:

Three families corresponding to the families of interest:

Sulfated arabinogalactan (*Codium fragile*)

Apiogalcturonan (*Zostera marina*)

Sulfated heteroglycan (*Caulerpa racemosa*)

Two other families by way of comparison:

Carrageenans (*Agardhiella t*) known for their activity against the influenza virus Ulvan (*Ulva a*)

The results of biological activity of the polysaccharides tested are presented in FIGS. 6 and 7.

The polysaccharides 79, 98, 109, 141, 237, 239, 240 and 242 belong to the sulfated arabinogalactan family. The polysaccharide 138 belongs to the apiogalacturonan family. The polysaccharides 233 and 234 belong to the sulfated heteroglycan family. The polysaccharides 164 to 166 belong to the carragheenan family and, finally, the ulvans are represented by the polysaccharides 244 and 245.

The polysaccharides, with the exception of the ulvans, demonstrated a strong biological activity with respect to the type B viruses. All the molecules inhibit more than 70% of the replication for a concentration of 250 µg/ml. The concentration which makes it possible to inhibit 50% of the viral replication is between 25 and 250 µg/ml for the apiogalacturonan 138 and is less than 2.5 µg/ml for all the sulfated arabinogalactans and sulfated heteroglycans.

The biological activity with respect to the type A viruses is much more reduced. However, the sulfated arabinogalactan polysaccharides and the heteroglycan sulfates which exhibit an activity with respect to this type are more effective than the control carrageenans. Thus, the sulfated arabinogalactans 79, 98, 109 and 141 inhibit between 25% and 75% of the viral replication when they are used at 250 µg/ml.

The results of biological activity of other polysaccharides are presented in FIGS. 8 and 9.

The polysaccharide 152 belongs to the sulfated arabinogalactan family, the polysaccharides 158, 160 and 161 to the apiogalacturonan family, and the polysaccharide 162 to the sulfated heteroglycan family. All these polysaccharides exhibit a strong activity with respect to the type A virus since, for a concentration of 250 µg/ml, the percentage inhibition is between 75% and 100%. The concentration which makes it possible to inhibit 50% of the viral replication is between 2.5 and 25 µg/ml. The polysaccharides 152 and 162 are also characterized by a strong activity with respect to the type B virus, with a concentration which makes it possible to inhibit 50% of the viral replication of less than 2.5 µg/ml. Although this concentration is between 2.5 µg/ml and 25 µg/ml, the polysaccharides 158, 160 and 161 also have a strong capacity for inhibiting the B viruses.

iii) By way of comparison, the activity of inulin, of rhamnose and of glucuronic acid cited as active agent in application WO 98/11778 were tested. Their activities are presented in the figures below. As shown by the results presented in FIGS. 10 to 15, none of these compounds exhibits any significant activity against the two influenza viruses tested.

b. Retrovirus-Like Particles i) The Importance of Retrovirus-Like Particles

The capacity of the surface glycoproteins of enveloped viruses to be incorporated onto viral particles originating from retroviruses was described a long time ago and is called "pseudotyping". Briefly, it is possible to control the incorporation of certain envelope glycoproteins of various viruses at the surface of recombinant retroviruses devoid of their own glycoproteins and carrying a defective genome which has a marker gene (in the present case, GFP or green fluorescent protein). Such hybrid viruses, or retrovirus-like particles (VLPs), therefore allow the infection of cells according to the receptors and routes followed by the parental viruses, the envelope glycoproteins of which are used. The list of glycoproteins capable of being incorporated at the surface of retroviral particles and of forming functional VLPs (i.e. VLP capable of infecting cells) is impressive (Sandrin V, et al. (2003) Targeting retroviral and lentiviral vectors. *Curr Top Microbiol Immunol.* 281:137-78) and includes numerous viruses originating from very distant families. The pseudotyping concept has resulted in several applications in the various sectors of biotherapeutic research, and more particularly in antiviral agent research. Indeed, by mimicking the cell-entry properties of the parental viruses from which the glycoproteins originate, VLPs allow numerous fundamental studies under low-containment conditions (L2, or even L1) even for class 4 viruses, owing to the fact that such hybrids are replication-defective. The infection by VLPs is limited to solely the step of cell entry and of integration of the recombinant genome, and induces the insertion of the genetic marker by virtue of the properties of the retroviral particle used (Nègre D, et al. (2000) Characterization of novel safe lentiviral vectors derived from simian immunodeficiency virus (SIVmac251) that efficiently transduce mature human dendritic cells. *Gene Ther.* 7:1613-23). Subsequently, quantitative measurement of the subsequent expression of the GFP marker gene by means of the cytofluorimetry technique makes it possible to very precisely determine the infectious capacity of the VLPs. VLPs are therefore particularly suitable for identifying compounds which have an antiviral effect due to an interference with the functions of the surface glycoproteins, for instance cell entry inhibitors.

ii) The Choice of Antigen

In the studies described below, retroviral particles pseudotyped with the surface glycoproteins of four different strains of the influenza virus were used. Incorporated at the surface of these VLPs were the two major glycoproteins of the influenza virus: hemagglutinin (HA) and neuraminidase (NA) (Bosch V, et al. (2001) Inhibition of release of lentivirus particles with incorporated human influenza virus haemagglutinin by binding to sialic acid-containing cellular receptors. *J Gen Virol.* 82:2485-94 and Sandrin V, et al. (2002) Lentiviral vectors pseudotyped with a modified RD114 envelope glycoprotein show increased stability in sera and augmented transduction of primary lymphocytes and CD34+ cells derived from human and nonhuman primates. *Blood.* 100:823-32). This made it possible to obtain an entirely functional conformation of these glycoproteins at the surface of the VLPs, in terms of viral entry. In these studies, two of the viral strains represent the highly pathogenic avian influenza: influenza A H5N1 and H7N1. The genetic constructs which allow the expression of the glycoproteins of these two avian influenza viruses have been described previously: "Fowl Plague Virus" (A/FPV/Rostock/34, H7N1, Ohuchi et al. (1994) Rescue of vector expressed fowl plague virus hemagglutinin in biologically active form by acidotropic agents and coexpressed M2 protein. *J Virol* 68:920-926, Hatziioannou T, et al. (1998) Incorporation of fowl plague virus hemagglutinin into murine leukemia virus particles and analysis of the infectivity of the pseudotyped retroviruses. *J Virol.* 72:5313-7 et Hatziioannou T, et al. (1999) Retroviral display of functional binding domains fused to the amino-terminus of influenza haemagglutinin. *Human Gene Therapy* 10:1533-44) and H5N1 (A/Thailand/1(KAN-1)/2004; Puthavathana et al., (2005) Molecular characterization of the complete genome of human influenza H5N1 virus isolates from Thailand. *J Gen Virol* 86:423-433 and Szécsi 3, et al. (2006) Induction of neutralizing antibodies by virus-like particles harboring surface proteins from highly pathogenic H5N1 and H7N1 influenza viruses. *Virol J* 3:70). The specific advantage of using FPV is that standardized infection/challenge trials are available in poultry and may be used to test the protection conferred by the candidate sugars. The development of VLPs with glycoproteins originating from the H5N1 virus is very relevant nowadays, given the current risk of pandemic.

Furthermore, VLPs which incorporate at their surface glycoproteins of two human strains of the influenza virus which regularly circulate in the population have been developed: influenza A H3N2 and an influenza B strain. This has made it possible to identify compounds which, in the future, may protect the human population in the event of an epidemic caused by these viruses.

iii) The Production of Retroviral Particles Pseudotyped with Influenza Virus Glycoproteins.

In order to produce viral particles pseudotyped with influenza virus glycoproteins, the mechanism of assembly of these glycoproteins on retroviral particles (Flu-VLP, Sandrin V, Cosset F L. (2006) Intracellular versus cell surface assembly of retroviral pseudotypes is determined by the cellular localization of the viral glycoprotein, its capacity to interact with Gag, and the expression of the Nef protein. *J Biol Chem.* 281:528-42) was used. Briefly, the influenza virus glycoproteins are incorporated at the surface of replication-deficient retroviruses originating from the murine leukemia virus (MLV). These Flu-VLPs consist of the GagPol proteins of MLV and a defective genone which has a GFP marker gene (Hatziiannou et al., 1998, Szécsi et al., 2006). The expression of GFP in the cells infected with these VLPs accurately reflects the infectious capacity of the glycoproteins at the surface of the VLPs. This system is therefore a very suitable tool for studying the cell entry and the inhibition of entry of influenza virus. The hemagglutinin (HA) and the neuraminidase (NA) of the various influenza viruses mentioned above were incorporated at the surface of VLPs. Flu-VLPs were produced by transient expression, in producer cells, of the internal (GagPol, GFP) and surface (HA, NA) viral components. The Flu-VLPs were harvested from the supernatant of the producer cells 48 h after transfection.

In order to evaluate the concentration of the Flu-VLP production, their infectious titer was determined, by adding serial dilutions of VLP carrying the GFP marker gene to TE671 cells (human rhabdomyosarcoma). The infectious titer was determined 72 hours after infection by measuring the percentage of GFP-positive cells by flow cytometry (FACS) as previously described (Nègre et al., 2000).

iv). Development of an Inhibition Test for Identifying Sugar Compounds with an Anti-Influenza Antiviral Activity Retroviral particles, carrying the GFP marker gene and incorporating, at their surface, glycoproteins originating from four influenza viruses mentioned above, were used to screen a library of sugars, in order to identify those which can effectively inhibit the entry of these influenza viruses. Various concentrations of sugars were incubated with the Flu-VLPs at 4° C. for 40 minutes. The sugar concentrations which were tested are: 500 µg/ml, 100 µg/ml and 10 µg/ml. After 40 min, the Flu-VLP-sugar mixture was brought into contact with TE671 cells, cooled beforehand to 4° C. The Flu-VLPs were left to bind to the cells for 2 h at 4° C. After this, the Flu-VLP-sugar mixture was removed, and the cells were rinsed with culture medium and then incubated in culture medium for 72 h at 37° C. The level of infectivity of the target cells, by FACS, was measured by taking advantage of the GFP expression in the infected cells (Bartosch B, et al. (2003) In vitro assay for neutralizing antibody to hepatitis C virus: evidence for broadly conserved neutralization epitopes. *Proc Natl Acad Sci USA* 100:14199-204). The % inhibition, which reflects the inhibition of the entry of the virus, was determined as the decrease in infectious titer in the presence of the sugar compared with the titer determined without the sugar.

This inhibition test is particularly sensitive and sound, and the results are reproducible. This test can be easily adapted to the 96-well plate format which can be easily analyzed with our cytometer (HTS/CantoII, Becton-Dickinson), which has an adapter for high sample throughput. This inhibition test was miniaturized in order to increase the screening capacity: the inhibition test was carried out in 96-well plates, which allowed us to test 96 different samples at a time.

v). Families of the Compounds which Inhibit Influenza Virus Entry: Retrovirus-Like Particle Model Arabinogalactans FIG. 16 presents the inhibitory activity of the sulfated arabinogalactans tested on the entry of influenza A H3N2 VLPs.

The majority of the sulfated arabinogalactans tested inhibited the entry of influenza A H3N2 VLPs (79, 237-240, 242), even at the lowest concentration (10 µg/ml). The inhibition efficacy was between 90% and 60%. The inhibition obtained with these sulfated arabinogalactan compounds was more effective than the inhibition with the control sugars, which were carrageenans.

FIG. 17 presents the inhibitory activity of the sulfated arabinogalactans tested on the entry of influenza B VLPs.

All the sulfated arabinogalactans tested, with the exception of 152, inhibited the entry of influenza B VLPs at concentrations of 500 and 100 µg/ml. The inhibition efficacy for the majority of these sugar compounds was between 90% and 60%. The inhibition obtained with these sulfated arabinogalactan compounds was more effective than the inhibition with the control sugars, which were carrageenans.

FIG. 18 presents the inhibitory activity of the sulfated arabinogalactans tested on the entry of influenza A H5N1 VLPs.

All the sulfated arabinogalactans tested inhibited the entry of influenza A H5N1 VLPs at concentrations of 500 and 100 µg/ml, and the majority were even effective at the concentration of 10 µg/ml. The inhibition efficacy for the majority of these sugar compounds was between 90% and 60%. The inhibition obtained with these sulfated arabinogalactan compounds was more effective than the inhibition with the control sugars, which were carrageenans.

FIG. 19 presents the inhibitory activity of the sulfated arabinogalactans tested on the entry of influenza A H7N1 VLPs.

All the sulfated arabinogalactans tested inhibited the entry of influenza A H7N1 VLPs at concentrations of 500 and 100 µg/ml. The inhibition efficacy for the majority of these sugar compounds was between 90% and 60%. The inhibition obtained with these sulfated arabinogalactan compounds was more effective than the inhibition with the control sugars, which were carrageenans.

In summary, a high entry inhibition efficacy was detected using the sulfated arabinogalactans, on the four types of influenza VLPs. The inhibition of viral entry was slightly more effective when the viral glycoproteins originated from highly pathogenic avian influenza viruses. The sulfated arabinogalactans were very effective for preventing viral entry, even at a low concentration (i.e. 10 µg/ml). The inhibition obtained with these sulfated arabinogalactan compounds was more effective than the inhibition with the control sugars, which were carrageenans. Moreover, it was demonstrated that the sulfation of the arabinogalactans was necessary in order to obtain the anti-influenza activity. FIG. 20 shows the % inhibitions of influenza A H5N1 VLP entry that were obtained with the sulfated arabinogalactans extracted from *Codium fragile* (79, 98, 109, 141, 152, 237, 238, 239, 240, 242) in comparison with those obtained in the case of two arabinogalactans extracted from *Codium fragile*, but which were desulfated (278, 279) and of a nonsulfated arabinogalactan extracted from larch (206). It is clearly apparent that, in the absence of sulfation, no activity is noted.

Apiogalacturonans

FIG. 21 presents the inhibitory activity of the apiogalacturonans tested on the entry of influenza A H3N2 VLPs. The two apiogalacturonan samples 160 and 161 inhibited the entry of influenza A H3N2 VLPs at concentrations of 500 and 100 µg/ml. The inhibition efficacy obtained with these sugars was between 50% and 60%.

FIG. 22 presents the inhibitory activity of the apiogalacturonans tested on the entry of influenza B VLPs. All the apiogalacturonan samples tested inhibited the entry of influenza B VLPs at concentrations of 500 and 100 µg/ml. The inhibition efficacy obtained with these sugar compounds was between 40% and 65%.

FIG. 23 presents the inhibitory activity of the apiogalacturonans tested on the entry of influenza A H5N1 VLPs. All the apiogalacturonan samples tested inhibited the entry of influenza A H5N1 VLPs at concentrations of 500 and 100 µg/ml. The inhibition efficacy obtained with these compounds was between 40% and 55%.

In summary, the efficacy of the inhibition of viral entry by the apiogalacturonans tested was moderate or high, depending on the VLPs used. Three types of influenza VLPs (H3N2, influenza B and H5N1) were inhibited by these sugars.

Sulfated Heteroglycans

FIG. 24 presents the inhibitory activity of the sulfated heteroglycans tested on the entry of influenza A H3N2 VLPs. All the sulfated heteroglycans tested inhibited the entry of influenza A H3N2 VLPs at concentrations of 500 and 100 µg/ml. The inhibition efficacy obtained with these sugar compounds was between 50% and 80%. The inhibition obtained with these sulfated heteroglycan compounds was similar to that obtained with the control sugars, which were carrageenans.

FIG. 25 presents the inhibitory activity of the sulfated heteroglycans tested on the entry of influenza B VLPs. All the sulfated heteroglycans tested inhibited the entry of influenza B VLPs at concentrations of 500 and 100 µg/ml. The inhibition efficacy obtained with these sugar compounds was between 90% and 65%. The inhibition obtained with these sulfated heteroglycan compounds was similar to that obtained with the control sugars, which were carrageenans.

FIG. 26 presents the inhibitory activity of the sulfated heteroglycans tested on the entry of influenza A H5N1 VLPs. All the sulfated heteroglycans tested inhibited the entry of influenza A H5N1 VLPs at concentrations of 500 and 100 µg/ml. The inhibition efficacy obtained with these sugar compounds was between 55% and 80%. The inhibition obtained with these sulfated heteroglycan compounds was similar to that obtained with the control sugars, which were carrageenans.

FIG. 27 presents the inhibitory activity of the sulfated heteroglycans tested on the entry of influenza A H7N1 VLPs. All the sulfated heteroglycans tested inhibited the entry of influenza A H7N1 VLPs at concentrations of 500 and 100 µg/ml. The inhibition efficacy obtained with these sugar compounds was between 60% and 80%. The inhibition obtained with these sulfated heteroglycan compounds was similar to that obtained with the control sugars, which were carrageenans.

In summary, a very high influenza VLP entry inhibition efficacy was obtained using the sulfated heteroglycans on the four types of VLP.

Carrageenan (Positive Control Sugars)

FIG. 28 presents the inhibitory activity of the carrageenans tested on the entry of influenza A H3N2 VLPs. All the carrageenans tested inhibited the entry of influenza A H3N2 VLPs at concentrations of 500 and 100 µg/ml. The inhibition efficacy obtained with these sugar compounds was between 60% and 70%. The inhibition obtained with these carrageenans was less than that obtained with the sulfated arabinogalactans.

FIG. 29 presents the inhibitory activity of the carrageenans tested on the entry of influenza B VLPs. All the carrageenans tested inhibited the entry of influenza B VLPs at concentrations of 500 and 100 µg/ml. The inhibition efficacy obtained with these sugar compounds was between 90% and 80%. The inhibition obtained with these carrageenans was less than that obtained with the sulfated arabinogalactans.

FIG. 30 presents the inhibitory activity of the carrageenans tested on the entry of influenza A H5N1 VLPs. All the carrageenans tested inhibited the entry of influenza A H5N1 VLPs at concentrations of 500 and 100 μg/ml. The inhibition efficacy obtained with these sugar compounds was between 90% and 80%. The inhibition obtained with these carrageenan compounds was less than that obtained with the sulfated arabinogalactans.

FIG. 31 presents the inhibitory activity of the carrageenans tested on the entry of influenza A H7N1 VLPs. All the carrageenans tested inhibited the entry of influenza A H7N1 VLPs at concentrations of 500 and 100 μg/ml. The inhibition efficacy obtained with these sugar compounds was between 60% and 80%. The inhibition obtained with these carrageenan compounds was less than that obtained with the sulfated arabinogalactans.

In summary, a very level of entry inhibition was obtained with the carrageenans, on the four types of influenza VLP. Nevertheless, the carrageenans were only effective at high concentrations (500 and 100 μg/ml), and the entry inhibition efficacy was lower than that obtained with the sulfated arabinogalactans.

iv) In Vivo Results

The anti-influenza activity of the sulfated arabinogalactan polysaccharide (294), of the sulfated heteroglycan polysaccharide (295) and of the apiogalacturonan polysaccharide (296) is evaluated in a murine influenza infection model.

Ethical Considerations

Specific pathogen-free, 6-8-week-old female BALB/c mice (16-20 g) were provided by Charles Rivers Laboratories (France). The mice underwent an acclimation and observation period of more than 48 h (before inoculation of the virus) making it possible to discard any animals showing signs of diseases and/or physical anomalies. All the animal care and experimental procedures were approved by the animal ethics committee of the University of Lyons.

Protocol of In Vivo Experiments

FIG. 32 presents the effect of the treatments with the sulfated arabinogalactan polysaccharide 294, with the sulfated heteroglycan polysaccharide 295 and with the apiogalacturonan polysaccharide 296 on the survival of mice infected with the influenza H1N1 A/Puerto Rico/8/34 virus (25 MLD50). The polysaccharides were administered orally in a single application of 20 mg/kg 4 hours after the inoculation of the virus and then, 24 hours after the inoculation, twice a day by application of 10 mg/kg.

The mice were anesthetized with isoflurane and exposed, by intranasal instillation, to 20 μl of various dilutions, in a phosphate buffered saline (PBS), to 1/10 of an influenza A (H1N1) A/Puerto Rico/8/1934 virus. The 50% lethal dose (MLD50) of the virus was calculated after an observation period of 14 days.

Three groups of 5 mice were formed for evaluating the activity of each of the polysaccharides: 1) group not infected and treated with the polysaccharide, 2) group infected and not treated with the polysaccharide, 3) group infected and treated with the polysaccharide.

The mice of the infected groups were obtained after nasal administration, under an anesthesia with isoflurane, of the viral load corresponding to 25 MLD50.

Four hours after the viral inoculation, the mice of the groups infected and treated with the polysaccharide received a single administration of 20 mg/kg nasally or orally (per os), and then, 24 hours after infection with the virus, 10 mg/kg twice a day for 3 days. The nontreated groups received a corresponding administration of saline solution (polysaccharide vehicle).

In this murine model of influenza A infection, the influenza infection leads to the death of the animals in a few days, preceded by a weight loss. Thus, the antiviral activity is evaluated over a period of 14 days by measuring the following parameters: weight loss, reduction in mortality and/or increase in survival time (mean day to death: MDD).

The treatment with the sulfated arabinogalactan polysaccharide 294, the sulfated heteroglycan polysaccharide 295 and the apiogalacturonan polysaccharide 296 makes it possible to reduce the morality of the animals infected with the influenza A H1N1 A/Puerto Rico/8/34 virus. While the percentage survival is 0% in the infected nontreated group, the percentage survival in the groups infected and treated with the sulfated arabinogalactan, sulfated heteroglycan and apiogalacturonan polysaccharides is 20%, 40% and 20%, respectively.

The treatments with the sulfated arabinogalactan and apiogalacturonan polysaccharides are also effective for preventing weight loss in the infected animals and they make it possible to increase the MDD by 1 day. Specifically, the MDD of the infected nontreated group is 6 days, whereas the MDDs of the groups infected and treated with the sulfated arabinogalactan and apiogalacturonan polysaccharides are 7 days, as shown in FIG. 32.

3. Mechanism of Action

The results obtained in the modeling of viral entry by the VLPs, set out in Section 2, demonstrate that the sulfated arabinogalactan sugars, the apiogalacturonans and the heteroglycan sulfates can have a preventive effect, in addition to a curative effect against influenza viruses.

Other tests were carried out a) to demonstrate sugar-hemagglutinin interactions and b) on an example of MOA during the viral cycle.

a. Demonstration of the Sugar-Hemagglutinin Interactions

The study of the mechanisms of action of the polysaccharides of interest is carried out by means of a screening platform using sugar chip technology.

This technology—which requires prior chemical functionalization of the sugars before their immobilization—coupled to a method of detection by Surface Plasmon Resonance imaging (SPRi) is a relevant method for studying, in real time and without labeling of biomolecules, the interactions between the immobilized polysaccharides and proteins in solution.

For the screening of the sugar families described in the present invention, the ligand selected is the hemagglutinin (HA) envelope glycoprotein, more specifically the HA1 soluble subunit, required for attachment of the influenza virus to the host cell.

The SPR studies made it possible to demonstrate a specific and dose-dependent interaction between these sugars and the purified HA1 protein, and underline that the antiviral action of these polysaccharides is carried out by inhibition of the binding of the viral envelope to its receptor.

This work is illustrated for various sugars belonging to the following families:

Apiogalacturonan polysaccharides: 158, 160, 161, 138
    Arabinogalactan polysaccharides: 79, 98, 109, 141, 237, 239, 240, 242
    Sulfated heteroglycan polysaccharides: 162, 233, 234
    Efficacy control: carrageenan polysaccharides: 164, 165, 166 i. Chemical Functionalization of the Sugars

The covalent immobilization of the sugars on a gold surface requires them to be chemically functionalized beforehand. While numerous functions are available on the carbohydrate chain, the aldehyde function of the reducing end has the advantage of being unique, and coupling on this position makes it possible to orient the sugars in the same way on the surface.

The chemical coupling is carried out in two steps. First, the sugars are modified with a bifunctional reagent, dihydrazide adipate, the free primary amine function of which can then react with a molecule of pyrrole branched with an activated ester chain (pyrrole NHS). The general principle of the coupling is summarized in FIG. 33.

1. Coupling of the Polysaccharides with Dihydrazide Adipate

The pyranose form of the sugar located at the reducing end is in equilibrium with a minor open tautomeric form, which has an aldehyde function. It is this function which reacts firstly with the hydrazide of the dihydrazide adipate, in an acidic medium. This step, limited by the degree of ring opening of the monosaccharides (1% of open form), is determined. During the reaction, an equilibrium toward the cyclic form of the sugar is favored, thereby making it possible to recover the native form of the monosaccharide.

In order to carry out the coupling, 4 mg of polysaccharides, accurately weighed, are dissolved in 1.8 ml of 0.1 M sodium acetate reaction buffer, pH 5, to which 200 µl of a stock solution of dihydrazide adipate at 500 mM are added. The reaction is carried out at 56° C. for 72 hours. For each polysaccharide coupled, a control condition, without dihydrazide adipate is carried out in parallel. At the end of this coupling, purification by dialysis against $H_2O$ makes it possible to dispense with the salts and the unreacted reagent. The sugars are then concentrated, lyophilized and weighed in order to determine the amount of total sugar recovered.

2. Coupling of the "Polysaccharide-Hydrazide" with N-Hydroxysuccinimidyl-6-(Pyrrolyl)-Caproate (Pyrrole-NHS)

In a second step, the sugars react with N-hydroxysuccinimidyl-6-(pyrrolyl)-caproate (synthesized as in 1), by means of an elimination addition reaction between the activated ester and the free hydrazine function of the dihydrazide adipate arm of the sugar.

This reaction must take place in a 50% PBS/50% DMSO v/v buffer, in order to promote the solubility of the pyrrole-NHS, without precipitating the polysaccharide.

The sugars functionalized with the dihydrazide adipate are taken up in PBS at 20 mg/ml. 100 µl of sugar, 60 µl of DMSO and 40 µl of a 50 mM stock solution of pyrrole-NHS (in DMSO) are mixed together. The reaction is carried out for 2 hours, at ambient temperature.

Control conditions, with the unmodified sugars, are also carried out. At the end of the reaction, the reaction volume is made up to 500 µl with 50% PBS/50% DMSO v/v buffer, and a step of dialysis against this buffer makes it possible to remove the remaining pyrrole-NHS. The salts are then removed by dialysis against $H_2O$. Finally, the sugars are lyophilized and accurately weighed. They are taken up at 20 mg/ml in water.

3. Estimation of the Coupling Yield

A colorimetric assay makes it possible to obtain an estimation of the coupling yield of the two reactions, and thus to be able to graft the various polysaccharides of interest onto the surface at one and the same pyrrolylated sugar concentration. This method, using the TNBSA reagent (P2297-10 ml, Sigma-Aldrich), is based on the detection of the primary amines and hydrazines. It makes it possible, after the first coupling reaction, to determine the proportion of sugars coupled with the dihydrazide adipate, and after the second reaction, to estimate the amount of pyrrolylated sugar, by measuring a decrease in the hydrazines in the solution. The detection is carried out at 450 nm (Victor 1420 Multilabel Counter), and the quantification is estimated by means of a calibration range prepared with various solutions of dihydrazide adipate. In a 96-well plate, 10 µl of sample (modified or unmodified sugar) or of calibration range are added to 40 µl of 0.1M $Na_2CO_3/NaHCO_3$ buffer, pH 9.6. 10 µl of TNBSA reagent diluted to 1/10th in this buffer are added to each well. After incubation for 4 minutes, the colorimetric reaction is stopped by adding 100 µl of 98.5% 0.1 M $NaH_2PO_4/1.5\%$ 0.1 M $Na_2SO_4$ v/v stop buffer, and the absorbance is read.

ii. Immobilization of the Sugars: Electrospotting

The covalent immobilization of the "polysaccharide-pyrrole" molecules is carried out by electrocopolymerization with pyrrole monomers. This process, called electrospotting, allows very rapid grafting of a biomolecule onto a gold surface via a polypyrrole film (Livache T, et al. Synth. Met, 2001, 121 (2-3):1443-1444).

The chips consist of glass prisms (n=1.717 at λ•=633 nm) coated with a thin layer of gold (50 nm) (Genoptics, Orsay). The protocol, described by Mercey et al. (Methods Mol Biol. 2007 385:159-75), consists in preparing reaction mixtures containing pyrrole at 20 mM and the pyrrolylated sugars at various concentrations (5 and 50 µM), in electrocopolymerization buffer (50 mM $NaH_2PO_4$, 50 mM NaCl, 10% (w/v) glycerol, pH 6.8). The construction of the chip is then carried out using a robotic device (Genomic solutions) and a U12 acquisition board (LabJack), controlled by Labview software. The electrochemical system consists of a ceramic pin (X-Tend Pin, Genoptics) containing a 200 µm platinum wire, capable of sampling the solutions of pyrrolylated sugars contained in a 96-well plate and depositing them at a precise site on the prism. A pulse with a voltage of 2.4 V lasting 100 ms between the pin (counterelectrode) and the gold surface (working electrode) causes the synthesis of the polypyrrole film and the deposition thereof on the surface. When all the spots have been synthesized, the prism is rinsed with water, dried and stored at 4° C.

An illustration of the diagram for depositing the spots on the gold-plated surface of a prism is given in FIG. 34. Shown on the left of FIG. 34 is the differential image obtained by SPR, during the injection of HA1 (H1N1) at 600 nM. Family A: apiogalacturonans; family B: sulfated arabinogalactans; family C: sulfated heteroglycans; family D: carrageenans; family E: glucomannans; Hp: 15 kDa heparin; PPy: polypyrrole.

120 spots are grafted onto the surface, representing 29 polysaccharides of 5 families at two concentrations (5 and 50 µM of pyrrolylated sugar), in duplicate.

Functionalized 15 kDa heparin (HP) (Sigma) is also deposited and serves as a positive control for the deposition, the injection of one of the known ligands of this sugar, interferon-γ (IFNγ) (Sarrazin S, et al. (2005) J Biol. Chem 280: 37558-64) making it possible to verify the presence of the grafted sugar.

Four polypyrrole spots are also deposited, and serve as negative controls.

iii. Study of the Interactions Between HA1 and the Polysaccharides by SPRi

1. Hemagglutinin Purification

Hemagglutinin HA is a homotrimer of 220 kDa which is present at the surface of influenza viruses and responsible for their attachment to target cells via its binding to the sialic acids attached to the glycoproteins and glycolipids of the host (Skehel J J, Wiley D C. (2000) Receptor binding and membrane fusion in virus entry: the influenza hemagglutinin. Annu Rev Biochem 69: 531-69). Each monomer is composed of two subunits, linked to one another via a disulfide bridge:

HA1 and HA2. HAL which is the soluble part of the protein, contains the receptor-binding site. The hemagglutinins included in these studies come from two extremely pathogenic avian influenza viruses: H5N1 and H7N1. Furthermore, the HA1 hemagglutinin of the H1N1 pandemic virus strain, which circulated in 2009 in the human population throughout the world, was included in this study. All the hemagglutinins were expressed as soluble proteins fused with a 6×His tag, allowing their purification. The proteins were produced by transient transfection in 293T human kidney cells. The soluble proteins were purified from the supernatant of the producer cells 48 hours after transfection. The purification of the various HA1s via their 6×His tag is carried out by means of a nickel-NTA column (Quiagen), and then with a gel filtration column (Superdex 75, GE Healthcare), in order to remove any contaminants. The purity of the protein was verified by migration on an SDS PAGE gel, followed by staining of the proteins with Coomassie blue, and also by Western blotting, visualization being carried out with an anti-His tag monoclonal antibody (Sigma) or an anti-HA1 antibody. The evaluation of the amount of protein collected is carried out by means of a colorimetric assay (QuantiPro BCA assay kit, Sigma-Aldrich), and the proteins are stored at 4° C.

2. HA1-Polysaccharide Interactions

The interactions between the purified protein and the sugars of interest, immobilized on the chip, are studied by real-time SPRi without prior labeling of the molecules. The optical system (Genoptics), described by Mercey E, et al. (2008) Anal Chem 80:3476-82 and Guedon P, et al, (2000) Anal Chem 72:6003-9, makes it possible to directly visualize the interactions on each spot, and to obtain the polysaccharide-protein complex association and dissociation curves by means of Genovision software (Genoptics).

The interactions take place inside a 7.2 μl PEEK interaction cell, connected to a syringe-driver pump, in the rinsing buffer (10 mM HEPES, 150 mM NaCl, 0.005% Tween 20, pH 7.4) delivered at a flow rate of 70 μl/min. All the buffers used for these experiments are filtered and degassed beforehand. Before each interaction study, the prism is saturated by an injection of rinsing buffer containing 1% (w/v) of BSA. After the injection of the protein over the course of 7 minutes, the surface is rinsed with rinsing buffer in order to remove the unbound molecules and to dissociate the complexes. The regeneration is carried out with rinsing buffer containing 1M NaCl, or else 2M guanidine-HCl, for 5 minutes.

The proteins are injected at increasing concentrations, ranging from 50 nM to 800 nM.

In FIG. 34, the image on the left represents the prism seen in SPR imaging, during the injection of the HA1 (H1N1) protein at 600 nM. The values of the percentage reflectivity of each species—sugar or pyrrole, which is the negative control of our experiments—are noted at the end of injection of the protein.

The results are symbolized in the form of histograms, representing the percentage reflectivity of the sugar (deposited at 50 μM) relative to the percentage reflectivity of the pyrrole (noted at the end of injection), for the protein concentration of 800 nM. These responses thus normalized make it possible to compare the interactions obtained for each of the polysaccharides studied. The more the value is above 1, the greater the interaction observed.

For a polysaccharide of each family, the curves of interaction (association and dissociation) with the three proteins, injected at various concentrations, are represented in FIGS. 35 to 41.

i. Studies of Interaction with the Arabinogalactans

FIG. 35 presents the curves of interaction of the sulfated arabinogalactans tested with the HA1 protein. All the sulfated arabinogalactans tested demonstrated a notable interaction with the purified hemagglutinins resulting from the three strains of virus studied. It may be noted, when the three proteins could be tested, HA1 (H5N1) is the one which shows the strongest interaction. The interactions observed are much stronger than those obtained between the HA1 proteins and the carrageenans, which are polysaccharides patented for their antiviral activity. FIG. 36 presents the curves of association and dissociation between the arabinogalactan 79 and the HA1 of the three influenza viruses, at various concentrations, while FIG. 37 presents the curves of association and dissociation between the pyrrole (negative control) and HA1 resulting from the three influenza viruses, at various concentrations.

The interactions observed between the hemagglutinins and the sugar 79, which serves as an example, are dose-dependent: the more the concentration of HA1 injected is increased, the greater the interaction. It was verified that this is not observed for the pyrrole spots (cf. above). The association phase is relatively rapid, whereas the dissociation of the complex takes place more slowly. Complete dissociation is obtained following an injection of 1M NaCl in the rinsing buffer or of 2M guanidine-HCl following the injection of the protein at the highest concentration.

ii. Studies of Interaction with the Sulfated Heteroglycans

FIG. 38 presents the curves of interaction of the sulfated heteroglycans tested with the HA1 protein. The sulfated heteroglycans which act in the biological tests also interact specifically with the purified HA1 proteins of the three strains of virus studied, and these interactions are greater than the carrageenans.

FIG. 39 presents the curves of association and dissociation between the sulfated heteroglycan 233 and the HA1 of the three influenza viruses, at various concentrations. As is illustrated with the polysaccharide 233, the interactions observed are specific and dependent on the concentration of protein injected (control, cf. pyrrole).

iii. Studies of the Interaction with the Carrageenans

FIG. 40 presents the curves of interaction of the carrageenans tested with the HA1 protein. The carrageenan polysaccharides, already described for their antiviral activity, serve as efficacy controls for the biological tests developed. However, it was noted by this sugar chip technology that the polysaccharides 164, 165 and 166 derived from this family do not interact or interact very little with the purified hemagglutinins. The interactions obtained are in fact weak, whereas the antiviral activities are similar to those of the other polysaccharides. It can therefore be assumed that the antiviral effect of these polysaccharides is not caused by binding with the HA glycoprotein of the virus envelope, but manifests itself with respect to another target.

FIG. 41 presents the curves of association and dissociation between the carrageenan 164 and the HA1 of the three influenza viruses, at various concentrations.

b. Example of MOA During the Viral Cycle

The mechanism of action was studied with the arabinogalactan 152. This polysaccharide was selected because of its strong activity, both with respect to the type A virus and with respect to the type B virus.

In order to determine the infectious cycle phases neutralized by the arabinogalactan 152, five infection modes were carried out so as to distinguish the early phases from the late phases of the infection.

The various tests were carried out in the presence of 30 CCID50/50 µl of virus for a final arabinogalactan 152 concentration of 62.5 µg/ml. The various modes used are summarized in FIG. 42.

Modes 1 to 4 make it possible to demonstrate an activity during the early phases of the infection. Mode 5 makes it possible to study an antiviral activity on the late phase of the infection.

FIGS. 43 and 44 represent the results of viral replication inhibition according to the five infection modes. Replication inhibition is mainly observable in mode No. 5, both in the presence of the A/Brisbane/10/07 virus and in the presence of the B/Florida/04/06 virus, showing that the molecule 152 mainly inhibits the end of the replicative cycle of the virus.

The invention claimed is:

1. A method of treating influenza in a human or an animal in need thereof comprising administering to said human or animal in need thereof a therapeutically effective amount of extract selected from the group consisting of a *codium fragile* extract, a *codium vermilara* extract, a *codium cylindricum* extract, a *zostera marina* extract, a *caulerpa racemosa* extract and mixtures thereof to treat the influenza in said human or animal.

2. The method of claim 1, wherein the extract contains at least one polysaccharide selected from group consisting of sulfated arabinogalactans, apiogalacturonans and heteroglycan sulfates, which are used as an antiviral agent against influenza.

3. The method of claim 2, wherein the antiviral activity against the influenza virus(s) is at least 70% provided by the sulfated arabinogalactans, apiogalacturonans or heteroglycan sulfates present.

4. The method of claim 2, wherein no compound, other than the sulfated arabinogalactan(s), the apiogalacturonans and the heteroglycan sulfates, exhibiting a significant antiviral activity, is administered to said human or animal for treating influenza.

5. The method of claim 2, wherein a therapeutically effective amount of an extract of *Codium fragile, Codium vermilara* or *Codium cylindricum* comprising sulfated arabinogalactanes is administered.

6. The method of claim 5, wherein the sulfated arabinogalactans have a size which is in the range of from 1000 to $2\times10^6$ g/mol, and/or a corresponding average load of from 2% to 50% of sulfate groups.

7. The method of claim 2, wherein a therapeutically effective amount of an extract of *Zostera marina* comprising apiogalacturonans is administered.

8. The method of claim 7, wherein the apiogalacturonans have a size which is in the range of from 10 000 to $10^6$ g/mol, and/or a corresponding average load of from 2% to 20% of sulfate groups.

9. The method of claim 2, wherein a therapeutically effective amount of an extract of *Caulerpa racemosa* comprising heteroglycan sulfates is administered.

10. The method of claim 9, wherein the sulfated heteroglycans have a size which is in the range of from 500 000 to $5\times10^6$ g/mol, and/or a corresponding average load of from 5% to 30% of sulfate groups.

11. The method of claim 1, wherein no olive oil, resveratrol, or extract of elderberry is administered to said human or animal, with the extract for treating influenza.

12. The method of claim 1, wherein the influenza is selected from human, avian, equine, porcine and feline influenza viruses.

13. The method of claim 1, wherein the extract is administered to a member of the avian population.

14. The method of claim 3, wherein the antiviral activity has at least 90%.

15. The method of claim 14, wherein the antiviral activity has at least 95%.

16. The method of claim 6, wherein the size is in the range of 3000 to $1.1\times10^6$ g/mol and/or the corresponding average load is from 5% to 40%.

17. The method of claim 8, wherein the size is in the range of 50,000 to 700,000 g/mol and/or the corresponding average load is from 4% to 12%.

18. The method of claim 10, wherein the size is approximately $10^6$ g/mol and/or the corresponding average load is from 13% to 22%.

* * * * *